US010023885B2

(12) United States Patent
Mohile et al.

(10) Patent No.: US 10,023,885 B2
(45) Date of Patent: Jul. 17, 2018

(54) PROCESS FOR THE PREPARATION OF PREGABALIN

(71) Applicant: HIKAL LIMITED, Pune (IN)

(72) Inventors: Swapnil Surendra Mohile, Pune (IN); Swapnil Gulabrao Yerande, Pune (IN); Sarika Madhukarrao Lunge, Pune (IN); Rameshkumar Maghabhai Patel, Pune (IN); Shivaji Balbhim Gugale, Pune (IN); Rajesh Mataprasad Thakur, Pune (IN); Ramesh Ananda Mokal, Pune (IN); Ashok Kumar Gangopadhyay, Pune (IN); Peter David Nightingale, Pune (IN)

(73) Assignee: Hikal Limited (IN)

( * ) Notice: Subject to any disclaimer, the term of this patent is extended or adjusted under 35 U.S.C. 154(b) by 29 days.

(21) Appl. No.: 14/434,658

(22) PCT Filed: Nov. 4, 2013

(86) PCT No.: PCT/IB2013/002435
§ 371 (c)(1),
(2) Date: Apr. 9, 2015

(87) PCT Pub. No.: WO2014/072785
PCT Pub. Date: May 15, 2014

(65) Prior Publication Data
US 2015/0344919 A1 Dec. 3, 2015

(30) Foreign Application Priority Data

Nov. 7, 2012 (IN) .......................... 3228/MUM/2012

(51) Int. Cl.
*C12P 7/62* (2006.01)
*C12P 13/00* (2006.01)
(Continued)

(52) U.S. Cl.
CPC .......... *C12P 13/001* (2013.01); *C07C 227/04* (2013.01); *C07C 227/30* (2013.01);
(Continued)

(58) Field of Classification Search
CPC .. C12P 7/40; C12P 13/002; C12P 7/42; C12N 9/18; C12N 9/78
(Continued)

(56) References Cited

U.S. PATENT DOCUMENTS

2010/0204503 A1 8/2010 Burns et al.

OTHER PUBLICATIONS

Liu et al. J. Mol Catalysis B, 2009, 56, pp. 126-130.*

(Continued)

*Primary Examiner* — Tekchand Saidha
*Assistant Examiner* — Mohammad Y Meah
(74) *Attorney, Agent, or Firm* — Brinks Gilson & Lione; Ryan L. Marshall; Jonathan Hartley

(57) ABSTRACT

The present invention provides an improved process for the preparation of a compound of formula (I), which comprises the steps of: formula (I), (a) reacting isovaleraldehyde of formula (II) and alkyl cyanoacetate of formula (III) optionally in presence of salts of weak acid and weak base or weak base in a suitable solvent to get 2-cyano-5-methyl-hex-2-enoic acid alkyl ester of formula (IV); (b) reacting 2-cyano-5-methyl-hex-2-enoic acid alkyl ester of formula (IV) with a suitable cyanide source in water or in an organic solvent or mixture thereof to get 2-isobutylsuccinonitrile of formula (V); (c) obtaining optionally 2-isobutylsuccinonitrile of formula (V) by reacting isovaleraldehyde of formula (II) and alkyl cyanoacetate of formula (III) in presence of suitable cyanide source in water or in an organic solvent or mixture thereof in single step; (d) converting 2-isobutylsuccinonitrile of formula (V) to racemic 3-cyano-5-methyl-hexanoic acid or salt thereof of formula (VI) with a genetically modified nitrilase enzyme (Nit 9N_56_2) in water or optionally with an organic co-solvent at appropriate pH and temperature; (e) converting racemic 3-cyano-5-methyl-hexanoic acid or salt thereof of formula (VI) to racemic alkyl 3-cyano-5-methyl-hexanoate of formula (VII) by treatment with alcohol (R3OH) and acidic catalyst or alkyl halide (R3X) in presence of a base in a suitable solvent or a mixture of solvents thereof; (f) obtaining (S)-alkyl 3-cyano-5-methyl-hexanoate of formula (VIII) and (R)-3-cyano-5-methyl-hexanoic acid or salt thereof of formula (X) by enzymatic enantioselective hydrolysis in water or organic solvent or a mixture thereof from racemic alkyl 3-cyano-5-methyl-hexanoate of formula (VII); (g) obtaining optionally the compound of formula (VII) by racemizing unwanted (R)-3-cyano-5-methyl-hexanoic acid or salt thereof of formula (X) or substantially enriched (R)-3-cyano-5-methyl-hexanoic acid salt thereof of formula (X) in presence of a base in organic solvent or a mixture thereof; (h) converting (S)-alkyl 3-cyano-5-methyl-hexanoate of formula (VIII) to pregabalin of formula (I) by hydrolyzing ester group with suitable alkali or alkaline earth metal base followed by hydrogenation optionally in one pot in a solvent selected from water or other organic solvents or a mixture thereof in presence of a suitable hydrogenation catalyst.

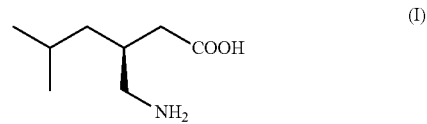

(I)

14 Claims, No Drawings

(51) Int. Cl.
*C07C 227/04* (2006.01)
*C07C 227/30* (2006.01)
*C07C 253/10* (2006.01)
*C07C 253/30* (2006.01)
*C12P 41/00* (2006.01)
*C12N 9/10* (2006.01)
*C12N 9/14* (2006.01)
*C12N 9/18* (2006.01)

(52) U.S. Cl.
CPC .......... *C07C 253/10* (2013.01); *C07C 253/30* (2013.01); *C12P 13/002* (2013.01); *C12P 41/005* (2013.01)

(58) Field of Classification Search
USPC ................................................ 435/128, 227
See application file for complete search history.

(56) References Cited

OTHER PUBLICATIONS

Gong et al. Microbial cell factories, 2012, 11, pp. 1-18.*
International Preliminary Report on Patentability for related International Application No. PCT/IB2013/002435, dated May 12, 2015 (12 pages).
International Search Report for Application No. PCT/IB2013/002435, dated May 9, 2014 (4 pgs).
Roy, Nath Bharab, et al., Eco friendly Industrial Process for Synthesis of (S)-3-(amino methyl)-5-methyl hexanoic acid (pregabalin), *Indian Journal of Chemistry* 51B: 1470-1488 (2012).
Tao, Junhua, et al., "Some Recent Examples in Developing Biocatalytic Pharmaceutical Processes," *Org. Process Res. Dev.* 12:392-398 (2008).

* cited by examiner

PROCESS FOR THE PREPARATION OF PREGABALIN

FIELD OF INVENTION

The invention relates to a commercially viable green process for manufacturing Pregabalin (1) in high yield with high chemical and chiral purity.

BACKGROUND

Pregabalin, chemically known as 3-(S)-(aminomethyl-5-methyl hexanoic acid having structure formula (1) is known to treat several central nervous system disorders that include epilepsy, neuropathic pain, anxiety and social phobia.

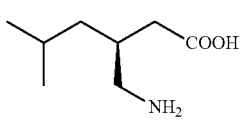
(I)

(S)-Pregabalin has been found to activate GAD (L-glutamic acid decarboxylase) in a dose dependent manner and promote production of GABA (gamma-aminobutyric acid), one of the major inhibitory neurotransmitters of brain. The discovery of antiseizure activity was first disclosed in U.S. Pat. No. 5,563,175.

Pregabalin has been prepared in various ways. One of the common approaches involves synthesis of racemic Pregabalin typically a 50:50 mixture of R and S isomers and subsequent resolution through diastereomeric salt formation. Such an approach could be found in Patent publications such as WO2009122215, WO2009087674, WO2009044409, WO 2008138874, WO2009125427 and WO2009001372. The major difficulties associated with this approach involve the loss of R-enantiomer along with a part of S-isomer as well and this can not be effectively recycled leading to cost pressure. Another approach has utilized resolution in the intermediate stage as a strategy. Scheme 1 outlines the approach described in WO 9638405. The synthesis involves Knovanagal condensation followed by Micheal addition and acidic hydrolysis gives diacid. The diacid was converted to mono amide which was resolved by (R)-phenylethylamine. After liberation of R-mono acid amide it was converted to (S)-Pregabalin by Hoffmann degradation. The overall yield was 12% and enantiomeric excess (ee) 99.8% over 8 steps. All commercially reagents were used and the chiral auxiliary can be recovered.

Scheme 1:

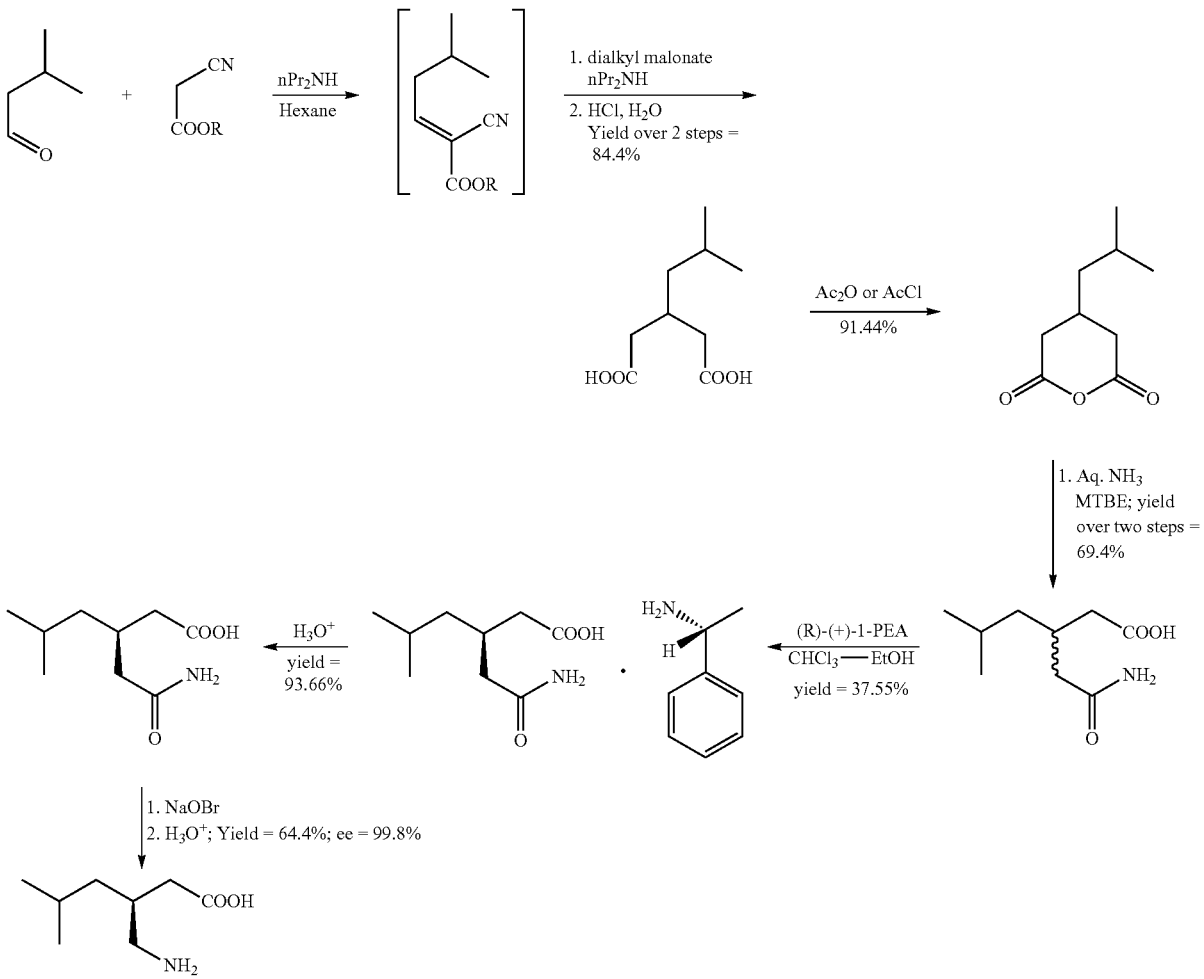

In WO2008137512, another approach described as shown in scheme 2, which involves resolution of amide intermediate followed by Hoffmann degradation.

Scheme 2:

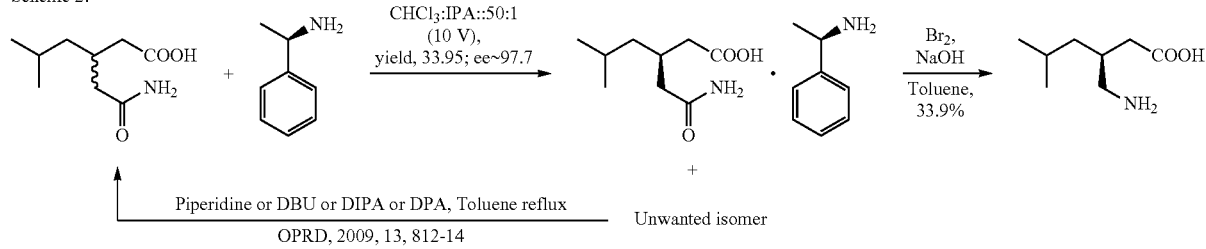

Piperidine or DBU or DIPA or DPA, Toluene reflux
OPRD, 2009, 13, 812-14

A further modification was described in OPRD, 2009, 13, 812-13. The approach described in patent publications WO2008062460 and U.S. Pat. No. 6,046,353 and is shown in scheme 3. This involves condensation of diethyl malonate with isovaleraldehyde followed by cyanation. The product is selectively hydrolyzed to cyano ester which on hydrolysis gave cyano acid. The cyano acid was hydrogenated to racemic Pregabalin. Finally it was resolved by using (S)-mandalic acid with overall yield of 15.5% and ee>99.5% over 6 steps.

Scheme 3

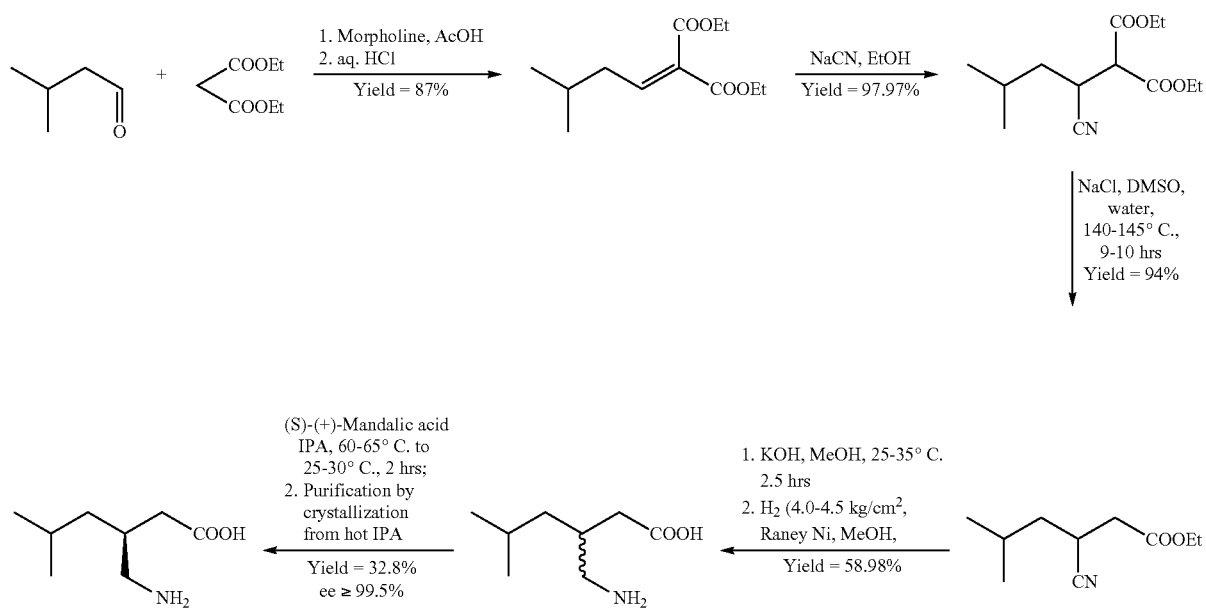

Another commonly used scaffold was found to be 3-isobutylglutaric acid anhydride (IBG). In US Patent publication No. 20090143615 and European Patent publication EP2067768 describes synthesis of Pregabalin as shown in scheme 4 that involves the ring opening by hydrazine followed by conversion to urethane acid by Curtius rearrangement. This intermediate was resolved using (S)-PEA. Release of chiral auxiliary followed by hydrolysis gave Pregabalin in overall yield of 12% over 4 steps with 99.8% ee. This method also suffers from the loss of unwanted R-isomer which can not be efficiently recycled.

Scheme 4:

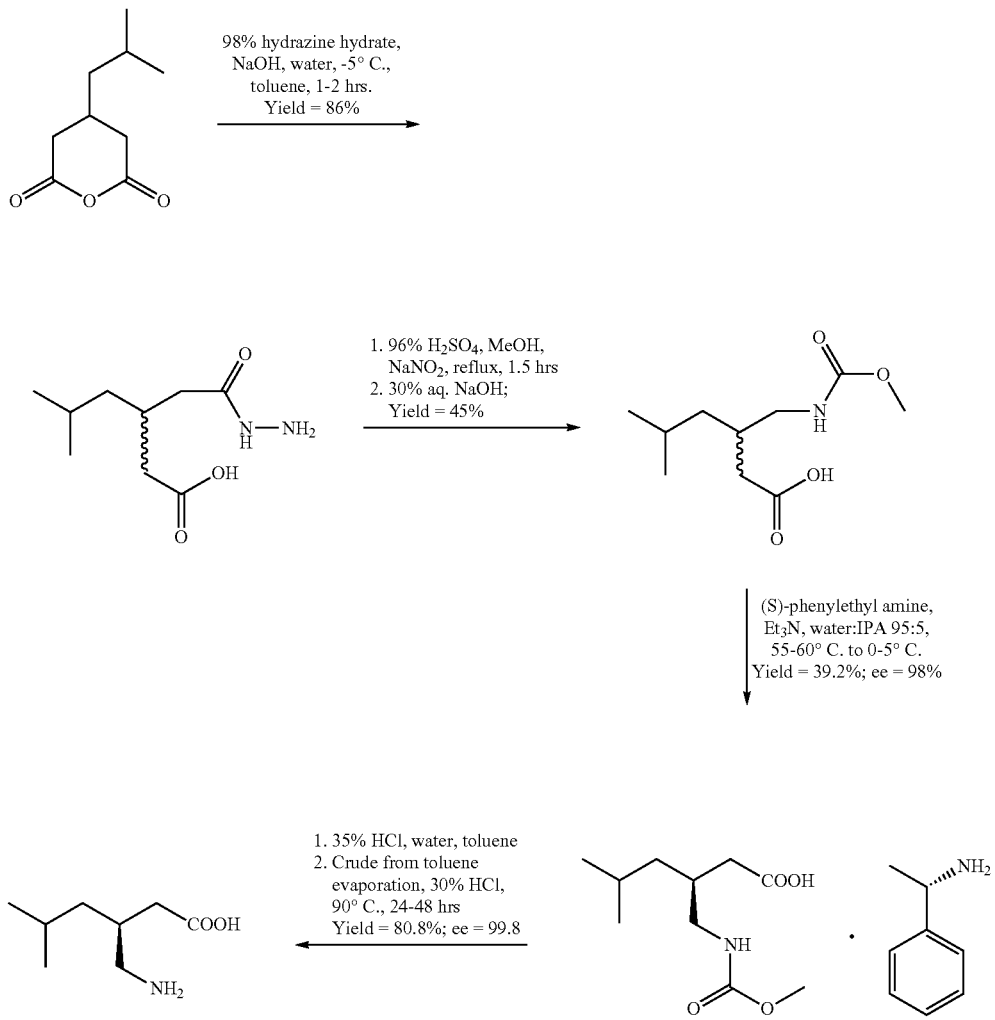

Asymmetric ring opening of IBG and subsequent chemical transformation to enantiopure Pregabalin constitute another approach. The Patent Publication WO2008118427 describes the synthesis of (S)-Pregabalin depicted in scheme 5, starting from 3-isobutyl-glutaric anhydride that involves the stereo selective ring opening with (S)-PEA with good yield and ee purity. This was converted to amide by mixed anhydride approach. The amide was subjected to Hoffman degradation followed by PEA amide hydrolysis in two different approach to form Pregabalin in 59.5 and 38.8% respectively with purity >99.5%.

Scheme 5:

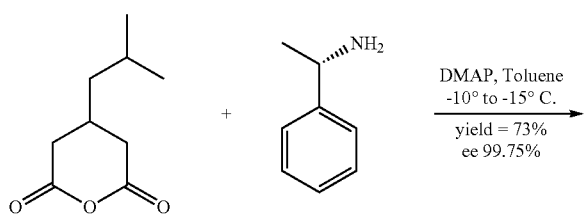

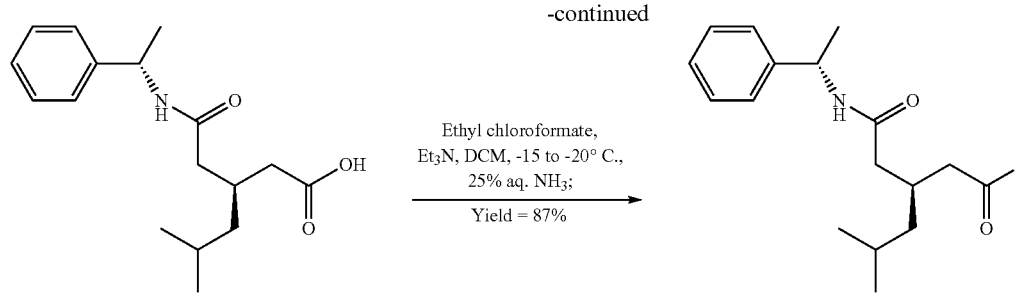

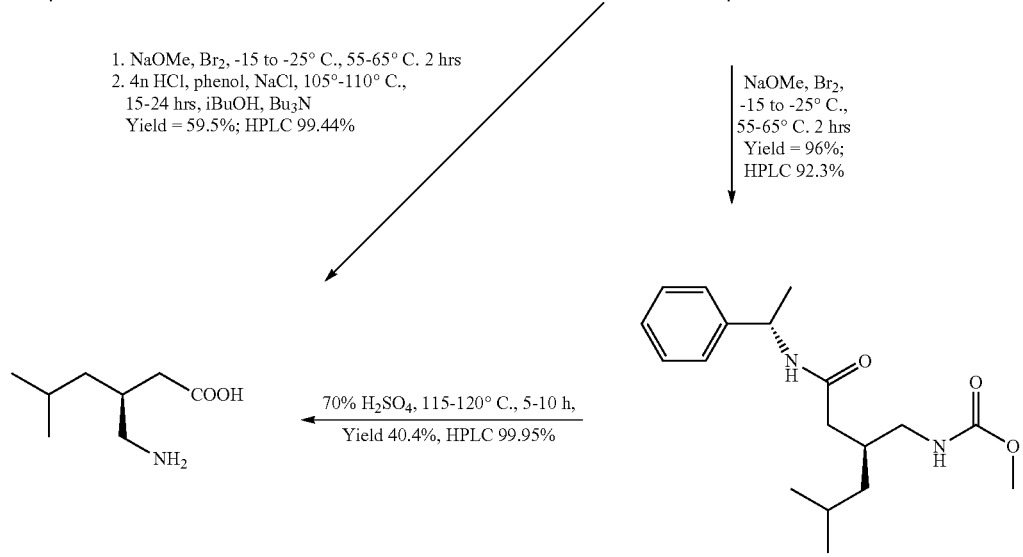

In a similar fashion, US Patent publication US 20070293694 described stereoselective ring opening of IBG with methanol in presence of molar equivalent of quinidine with high yield, however the ee is not satisfactory. Subsequent steps involve amidation followed by Hoffmann degradation. Use of molar equivalent of quinidine (expensive) and low ee makes the process unattractive.

Scheme 6:

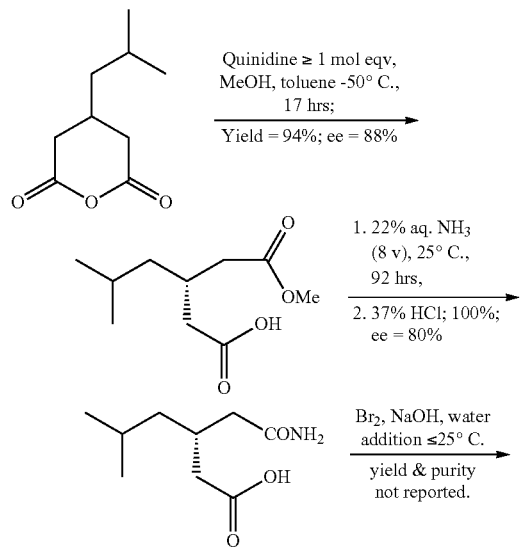

In yet another approach similar to that described in scheme 5, Patent publication WO2007035789 described stereo selective ring opening of 3-isobutyl-glutaric anhydride (IBG) with (R)-PEA as described in scheme 7. The chiral auxiliary was replaced by amide using alkali metal amide at low temperature followed by Hoffmann degradation to give (S)-Pregabalin in overall 32.9% yield in three steps.

Scheme 7:

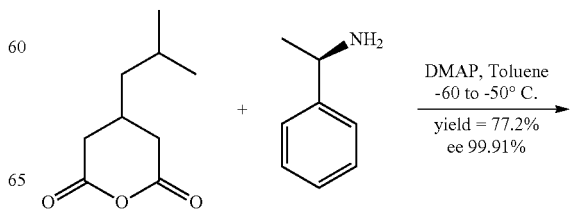

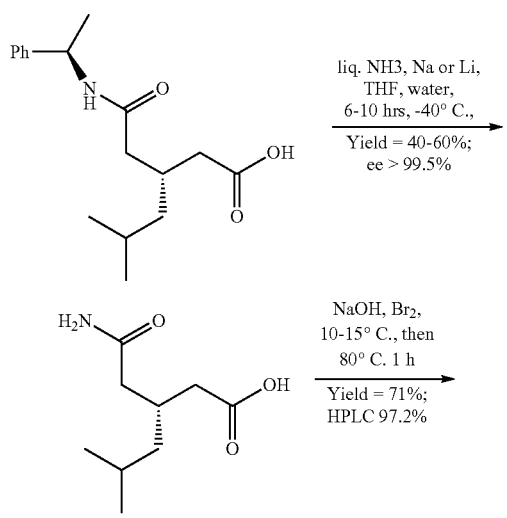

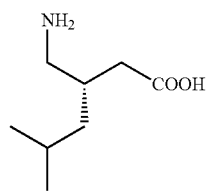

The synthesis reported in Patent publication WO2009081208 is shown in scheme 8. The ketone was converted to β-keto ester derivative which was converted to (S)-β-hydroxy intermediate by two different ways. The first method involve mauri yeast catalyzed reduction of ketone to give 50% yield and 99% ee while the second involve hydrogenation with [(S)—Ru (BINAP)Cl$_2$]$_2$·NEt$_3$ (0.00046 eq=0.44% w/w) in 66% yield and >99% ee. Another key step is the conversion of alcohol to inverted bromo using Br$_2$—PPh$_3$ and also involves chromatography. The bromo compound is again completely inverted to (S) configuration with nitromethane and 1,8-diazabicyclo[5.4.0]undec-7-ene (DBU). Hydrolysis of ester and hydrogenation of nitro completes the synthesis with an overall yield of 13% and ee>99% involving 6 steps.

Scheme 8:

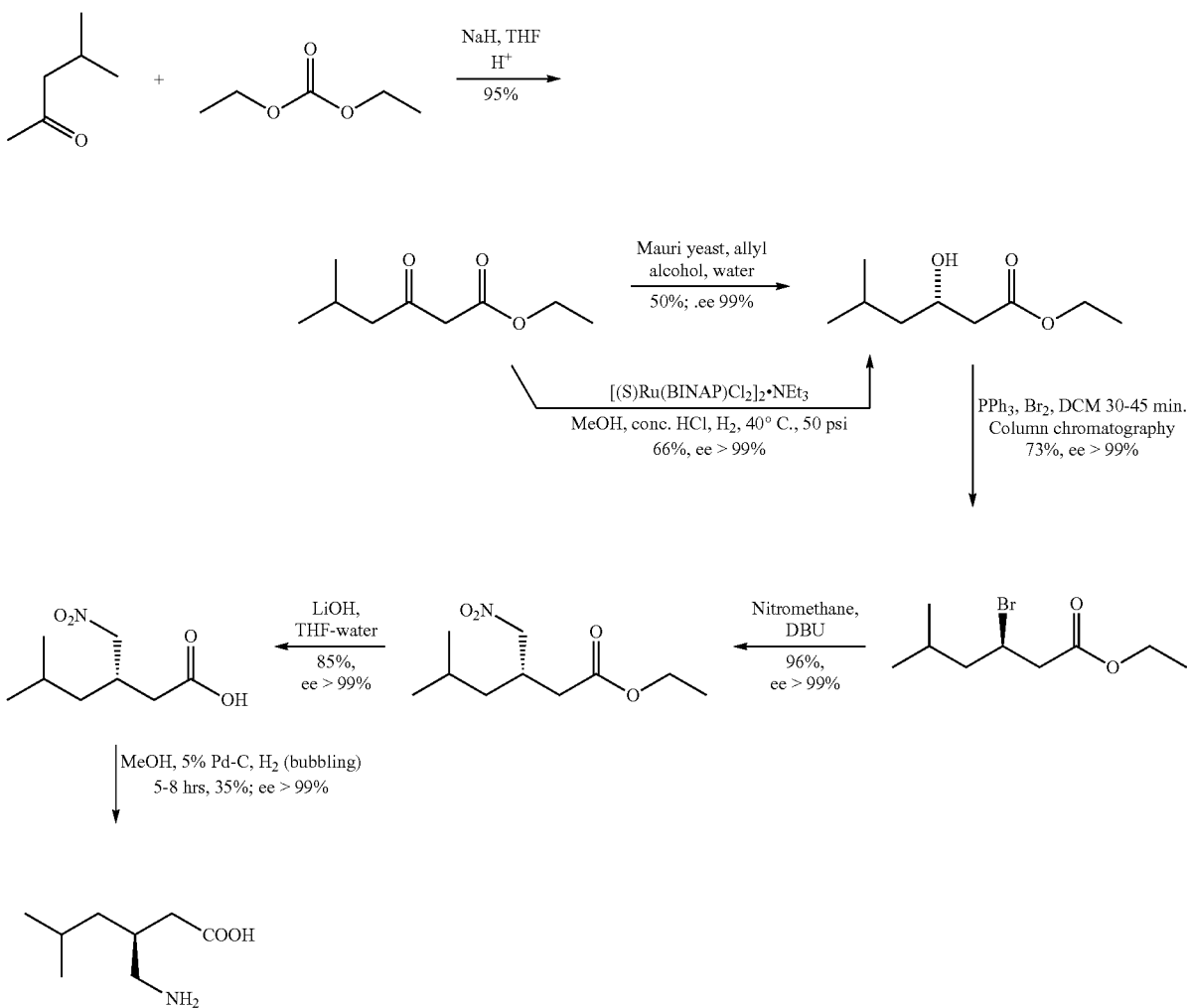

Another enzymatic route is shown in scheme 9 for the synthesis of Pregabalin was described in Patent publication US 20100204503. This involves kinetic resolution by lipase as the key step. The condensation of isovaleraldehyde with ethyl cyanoacetate followed by cyanation gave racemic dicyano compound. The Nitilase enzyme was used to get (S)-cyano acid and unwanted dinitrile which was racemized with DBU in toluene for recycling. The hydrogenation of (S)-tert butyl amine salt cyano acid gave (S)-Prgabalin in 7.7% overall yield with ~100% ee over 4 steps. The extremely poor yield at the final stage makes this process economically unviable.

Scheme 9:

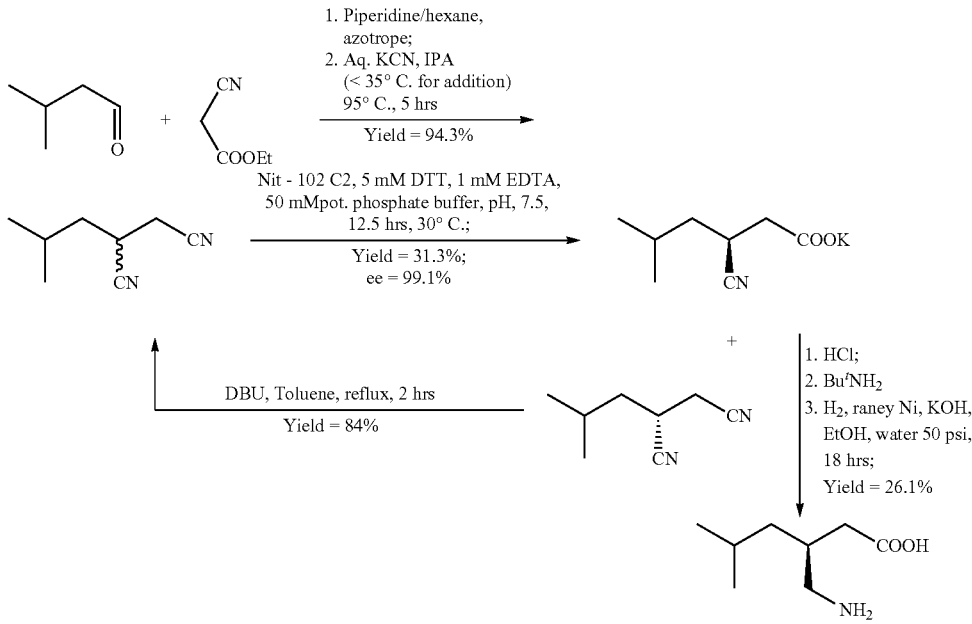

A rather more efficient enzymatic route is shown in scheme 10 was described in Patent publication US 2005028302. In this process the cyano diacid diethyl ester was enzymatically hydrolyzed to (S)-cyano ester monoacid potassium salt and the unwanted isomer was racemized. The salt was either reduced to a lactam acid followed by hydrolytic decarboxylation to Pregabalin with 34% overall yield and over 3 steps with ee>99.5%. Alternatively the (S)-cyano ester monoacid potassium salt was converted to cyano monoacid potassium salt that was hydrogenated to Pregabalin in 30% overall yield over 3 steps with 99.75% ee. Although it looks a reasonably good process however space vs. time yield will not be cost effective.

Scheme 10:

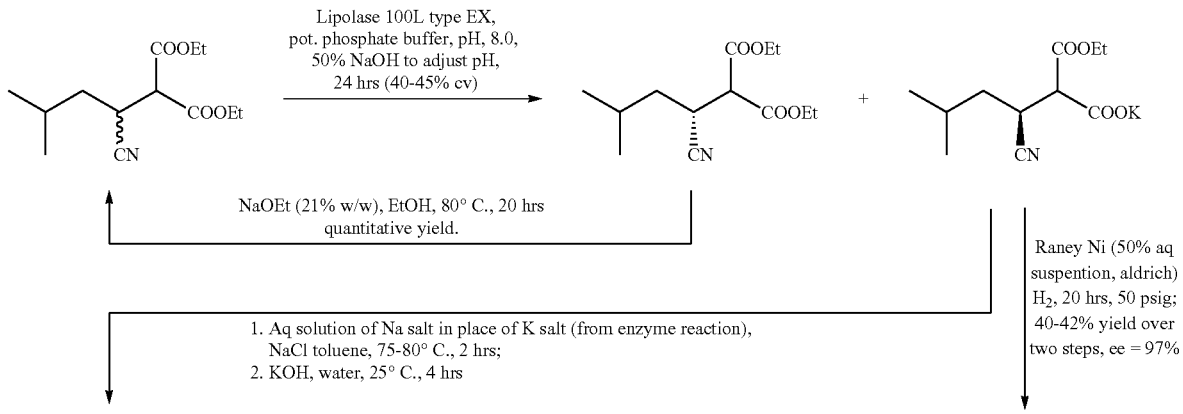

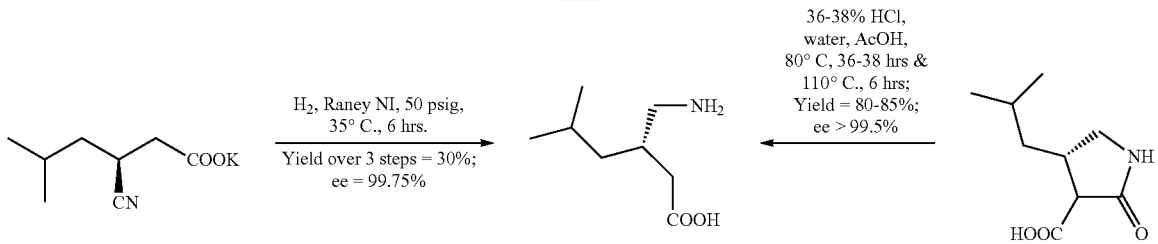

Finally there are some reports on asymmetric synthesis of Pregabalin mostly of academic interest due to the fact that they either involve longer sequence or provide Pregabalin with low ee. The scheme reported in J. Org Chem., 2003, 68, 5731-34 as shown in scheme 11, which described Bayllis-Hillman condensation and subsequent carbonate formation with chloroformate. The carbonate was subjected to CO insertion. The conjugated nitrile was hydrolyzed and converted to tert-butyamine salt that was stereo selectively hydrogenated to cyano acid using [(R,R)-(Me-DuPHOS)Rh(COD)].BF$_4$, followed by hydrogenation of CN with Ni to give Pregabalin in 41.5% overall yield with ee 99.8% over 6 steps.

Scheme 11:

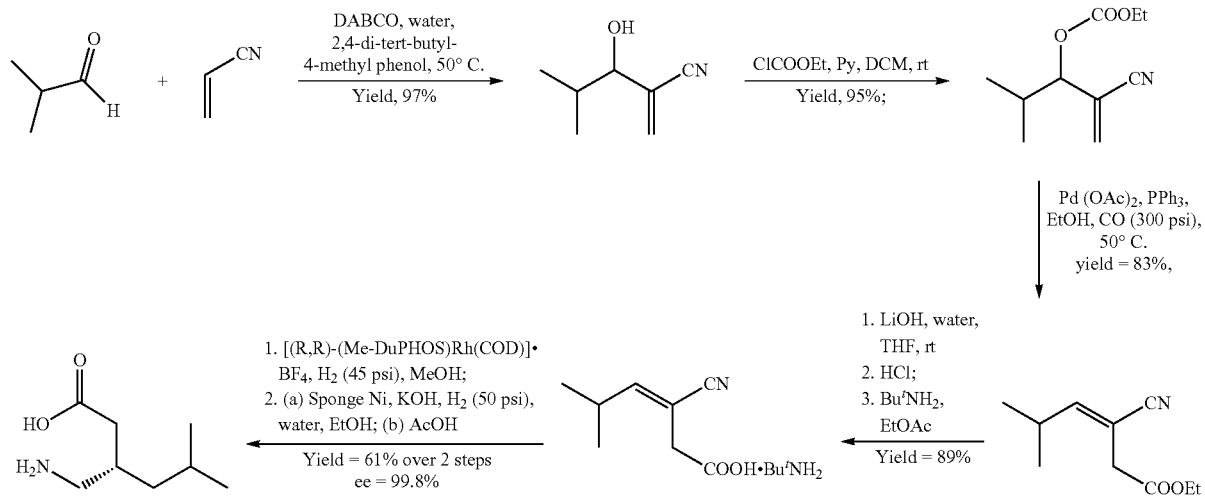

The synthesis described in Org. Lett., 2007, 9, 5307-09 as shown in scheme 12 involves asymmetric Micheal addition of nitromethane to αβ-unsaturated aldehyde using chiral catalyst. This catalyst need to be prepared from D-proline that involve 5 steps The number of steps are only three however ee is on the lower side. Additional resolution will be required Therefore this approach can not be economically viable.

Scheme 12:

-continued

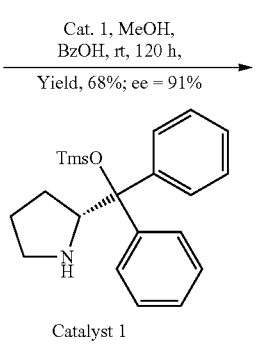

Catalyst 1

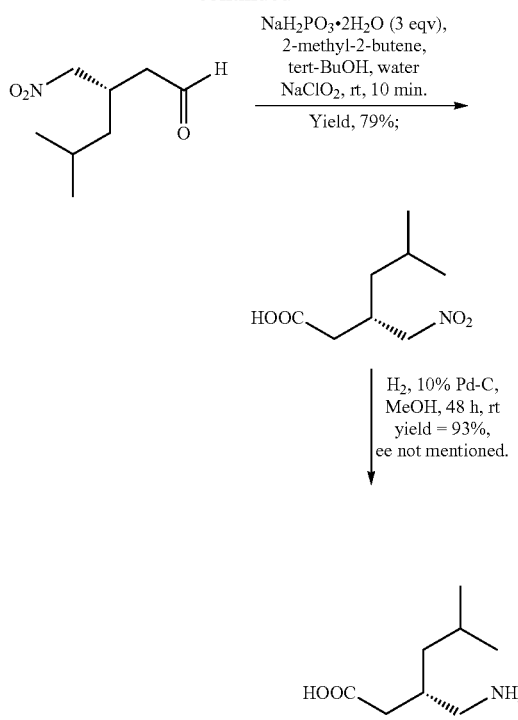

Based on the drawbacks mentioned in all the prior arts above, accordingly therefore, there is an urgent need to develop a process for the preparation of a compound of formula (I), which is readily amenable to scale-up. Hence, we focused our research to simplify the process for the preparation of a compound of formula (I) with greater yield, higher chemical and chiral purity by using a genetically modified nitralase enzyme as a biocatalyst in a substantially cost effective and eco-friendly manner and to obviate the problems associated with the prior art process(s).

OBJECTIVES OF THE INVENTION

The main object of the present invention is to provide a process for the preparation of a compound of formula (I), which is simple, economical, user-friendly and commercially viable.

Another objective of the present invention is to provide a process for the preparation of a compound of formula (I), which would be easy to implement on commercial scale, and to avoid excessive use of reagent(s) and organic solvent(s), which makes the present invention eco-friendly as well.

Yet another objective of the present invention is to provide a process for the preparation of a compound of formula (I) in a greater yield with higher chemical and chiral purity.

Still another objective of the present invention is to provide a process for the preparation of a compound of formula (I), wherein the byproduct formed during the reaction can be reusable and thereby recyclable, which makes the process industrially more suitable.

SUMMARY OF THE INVENTION

Accordingly, the present invention provides an improved process for the preparation of a compound of formula (I), which comprises the steps of:

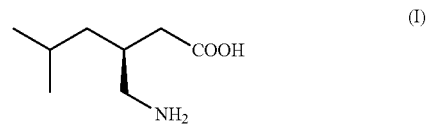

(a) reacting isovaleraldehyde of formula (II) and alkyl cyanoacetate of formula (III) optionally in presence of salts of weak acid and weak base or weak base in a suitable solvent to get 2-cyano-5-methyl-hex-2-enoic acid alkyl ester of formula (IV);

(b) reacting 2-cyano-5-methyl-hex-2-enoic acid alkyl ester of formula (IV) with a suitable cyanide source in water or in an organic solvent or mixture thereof to get 2-isobutylsuccinonitrile of formula (V);

(c) obtaining optionally 2-isobutylsuccinonitrile of formula (V) by reacting isovaleraldehyde of formula (II) and alkyl cyanoacetate of formula (III) in presence of suitable cyanide source in water or in an organic solvent or mixture thereof in single step;

(d) converting 2-isobutylsuccinonitrile of formula (V) to racemic 3-cyano-5-methyl-hexanoic acid or salt thereof of formula (VI) with a genetically modified nitrilase enzyme (Nit 9N_56_2) in water or optionally with an organic co-solvent at appropriate pH and temperature;

(e) converting racemic 3-cyano-5-methyl-hexanoic acid or salt thereof of formula (VI) to racemic alkyl 3-cyano-5-methyl-hexanoate of formula (VII) by treatment with alcohol ($R_3OH$) and acidic catalyst or alkyl halide ($R_3X$) in presence of a base in a suitable solvent or a mixture of solvents thereof;

(f) obtaining (S)-alkyl 3-cyano-5-methyl-hexanoate of formula (VIII) and (R)-3-cyano-5-methyl-hexanoic acid or salt thereof of formula (X) by enzymatic enantioselective hydrolysis in water or organic solvent or a mixture thereof from racemic alkyl 3-cyano-5-methyl-hexanoate of formula (VII);

(g) obtaining optionally the compound of formula (VII) by racemizing unwanted (R)-3-cyano-5-methyl-hexanoic acid or salt thereof of formula (X) or substantially enriched (R)-3-cyano-5-methyl-hexanoic acid salt thereof of formula (X) in presence of a base in organic solvent or a mixture thereof;

(h) converting (S)-alkyl 3-cyano-5-methyl-hexanoate of formula (VIII) to pregabalin of formula (I) by hydrolyzing ester group with suitable alkali or alkaline earth metal base followed by hydrogenation optionally in one pot in a solvent selected from water or other organic solvents or a mixture thereof in presence of a suitable hydrogenation catalyst.

The above process is illustrated in the following general synthetic scheme (13):

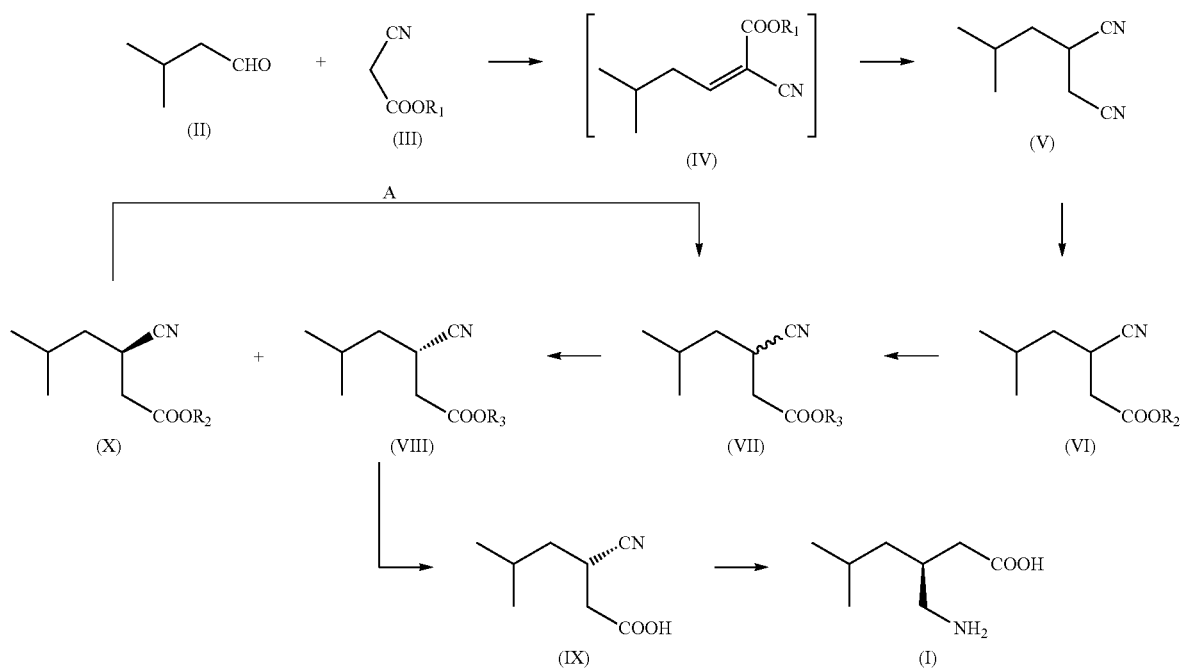

Wherein
$R_1$ = Linear or branched lower alkyl $C_1$ to $C_4$ and the like
$R_2$ = Cataionic counter ion, hydrogen, alkali metal salt, alkaline earth metal salt, ammonium salt, alkyl ammonium salt, organic amine salt and the like
$R_3$ = Linear or branched lower alkyl $C_1$ to $C_4$ or $C_7$ to $C_{10}$ aryl or alkyl aryl chain and the like
X = Any hallogen

DETAILED DESCRIPTION OF THE INVENTION

The present invention now will be described more fully hereinafter. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The words "racemate(s)" or "racemic mixture(s)" means the 50:50 mixtures of individual R and S enantiomers. The term "substantially pure S enantiomer (s)" indicates the presence of S enantiomer >>R enantiomer; preferentially the ratio of S:R can be in the range of 85:15 to 100:0; more preferably the ratio of S:R can be 95:5 to 100:0; while most preferably the ratio of S:R can be 99:1 to 100:0. The term "R Enriched enantiomer" indicates the presence of R enantiomer >>S enantiomer; preferentially the ratio of R:S can be in the range of 70:30 to 100:0.

In accordance with the objectives wherein the present invention provides an improved process for the preparation of a compound of formula (I) via selective enzymatic stereospecific synthetic approach.

Accordingly in an embodiment of the present invention wherein the said weak organic acid used in step (a) is preferably selected from the group consisting of benzoic acid, succinic acid maleic acid, fumaric acid, phthalic acid, acetic acid and the like more. The said weak base used in step (a) is preferably selected from the group consisting of triethyl amine, diisipropylethyl amine, pyridine, piperidine, 1,8-diazabicyclo[5.4.0]undec-7-ene and the like more preferably diisipropylethyl amine, piperidine. The said salts in step (a) is preferably selected from the group consisting of sodium acetate, ammonium acetate, ammonium benzoate, ammonium succinate, alkyl ammonium acetate and the like more preferably ammonium acetate, sodium acetate.

The crude compound of formula (IV) disclosed in step (a) can be used as such or can be purified by distillation by different techniques well understood by those skilled in the art.

In another embodiment of the present invention wherein the said suitable cyanide source of step (b) and (c) is preferably selected from the group consisting of lithium cyanide, sodium cyanide potassium cyanide, trimethylsilyl cyanide and the like, more preferably sodium cyanide or potassium cyanide. In another embodiment of the present invention wherein the reaction of step (b) the suitable cyanide source optionally can be used in 1-50% excess.

In another embodiment of the present invention wherein the said organic solvent in step (a) is preferably selected from the group consisting of ethyl acetate, dichloro methane, chloroform, methyl tert-butyl ether, cyclohexane, toluene and mixture thereof, more preferably cyclohexane or toluene.

In another embodiment of the present invention wherein the said reaction of step (a) and step (c) is carried out preferably at ambient temperature to reflux temperature, more preferably at reflux temperature.

In another embodiment of the present invention wherein the said organic solvent in step (b) and step (c) is preferably selected from the group consisting of water, ethyl alcohol, methyl alcohol, isopropyl alcohol, n-butyl alcohol, tetra hydrofuran, dioxane, dimethylformamide, dimethyl sulfoxide, dimethylacetamide, methyl tert-butyl ether, cyclohexane and the like and more preferably solvent is methyl alcohol or ethyl alcohol or water or a mixture thereof.

In another embodiment of the present invention wherein the reaction of step (b) preferably carried out at a temperature range between 45° C. to 120° C., more preferably 45° C. to 110° C. and the most preferably is at reflux temperature of the methanol to reflux temperature of water.

In another embodiment of the present invention wherein the said genetically modified nitrilase enzyme in step (d) is Nit 9N_56_2. In instant invention the present inventors were motivated to pursue the conversion of 2-isobutylsuccinonitrile of formula (V) to racemic 3-cyano-5-methyl-hexanoic acid or salt thereof of formula (VI) with the said enzyme with surprising selectivity, improved conditions, higher yields, minimum waste; therefore as a result promoting the green chemistry of preparation of a compound of formula (I).

In another embodiment of the present invention wherein the loading of compound of formula (V) for the preparation of compound (VI) in step (d) preferably can be chosen from 30 to 300 g per liter of water or water in combination of co-solvent; more preferably 50 to 200 g per liter of water or water in combination of co-solvent whilst most preferably 60 to 150 g per liter of water or water in combination of co-solvent.

In another embodiment of the present invention wherein the loading of said genetically modified nitrilase enzyme (Nit 9N_56_2) for the preparation of compound (VI) in step (d) preferably can be chosen from 4 to 25 U per g of compound (V) whilst more preferably 6 to 20 U per gram of compound (V) can be used.

In another embodiment of the present invention wherein during the preparation of compound of formula (VI) in step (d), the pH of the solution be kept in the range 7.2±0.8 and most preferably in the range of 7.0±0.5 and can be maintained by a suitable buffer and are well known in the art; one of the most preferred way to achieve is to use a phosphate or acetate buffer or maintain the pH with the addition of suitable acid chosen from among acetic, citric, tartaric, hydrochloric, sulfuric, phosphoric acid and the like whilst the most preferred acid is hydrochloric acid and or a base which is selected from the group consisting of ammonia, mono, di and tri alkyl amine, sodium hydroxide, sodium carbonate, potassium carbonate, sodium bicarbonate, potassium bicarbonate and the like, the most preferred base is sodium bicarbonate.

In another embodiment of the present invention wherein the substrate can be dispersed well with micronization or using dispesion stabilizing agent well known by those skilled in the art before loading of the said enzyme in step (d).

In another embodiment of the present invention wherein the reaction of step (d) preferably carried out at a temperature range between 25° C. to 40° C., more preferably 28° C. to 38° C. and the most preferably a temperature range between 30° C. to 37° C.

In another embodiment of the present invention wherein the said alcohol (R$_3$OH) in step (e) preferably is selected from the group consisting of methyl alcohol, ethyl alcohol, isopropyl alcohol, n-propyl alcohol, n-butyl alcohol, cyclopentanol, cyclohexanol and the like.

In another embodiment of the present invention wherein the said alkyl halide (R$_3$X) in step (e) preferably is selected from the group C$_1$-C$_5$ alkyl halides consisting of methyl iodide, ethyl chloride, ethyl bromide, ethyl iodide, n-propyl bromide, isopropyl chloride, isopropyl bromide and the like.

In another embodiment of the present invention wherein the said acid catalyst/or reagent in step (e) preferably is selected from the group consisting of hydrochloric acid, sulfuric acid, thionyl chloride, trimethylsilyl chloride, methanesulfonic acid, paratoluene sulfonic acid, benzene sulfonic acid, trifluoromethanesulfonic acid, Lewis acid or strongly acidic sulfonated resins well known in the art while most suitable catalyst and/or reagent is chosen from hydrochloric acid, sulfuric acid, paratoluene sulfonic acid, trimethyl silyl chloride and the like.

In another embodiment of the present invention wherein during the preparation of racemic alkyl 3-cyano-5-methyl-hexanoate of formula (VII) the same can be optionally purified by distillation in step (e).

In another embodiment of the present invention wherein the said enzymatic enantioselective hydrolysis in step (f) is performed by using commercially available hydrolysis enzymes such as esterasees, lipolases, lipases and the like. The said hydrolysis enzymes preferably is selected from the group consisting of *candida Antarctica* A, *candida Antarctica* B1, *candida Antarctica* BY2, Novozymes, Novozyme 435, *Rhizomucor meihei*, *Thermomyces lanhginosa*, *pseudomonas cepecia*, Resinase HT, Lipex 100L, *Bascillus subtillis*, lipase 3.101, lipase 3.102, lipase 3.104, lipase 3.105, lipase 3.106, lipase 3.107, lipase 3.108, lipase 3.109, lipase 3.111, lipase 3.115, lipase 3.113, lipase 3.117, lipase 3.136, AYS Amino, AS Amano, PS AmanoSD, AK Amano and the like while most preferred enzyme is *candida Antarctica* B1, *candida Antarctica* BY2, Novozyme 435.

In another embodiment of the present invention wherein the loading of preferred enzymes in step (f), is in the range of >0.1% to <5% w/w compared to the substrate; more preferably the range is 0.5% to 4% w/w compared to the substrate; whilst most preferably the range is 1.0% to 3% w/w compared to the substrate.

In another embodiment of the present invention wherein the preferred enzymes in step (f), may be recovered and reused for several times till almost full enzyme activity is retained; while during recycling of enzyme if the activity is less then additional amount of fresh enzyme can be added and the additional amount can be in the range of 5% to 50% w/w with respect to initial enzyme loading; more preferentially in the range of 5% to 25% w/w with respect to initial enzyme loading.

In another embodiment of the present invention wherein the said organic solvent in step (f) is selected from the group consisting of water, methyl alcohol, ethyl alcohol, isopropyl alcohol, n-butyl alcohol, isobutyl alcohol, acetone, methyl isobutyl ketone, acetonitrile, methyl tert-butyl ether, tetra hydrofuran, 2-methyl tetra hydrofuran, 1,4-dioxane, dimethyl sulfoxide, and the like and more preferably solvent is water, 1,4-dioxane, dimethyl sulfoxide or a mixture thereof.

In another embodiment of the present invention wherein during the preparation of compound of formula (VIII) in step (1), preferably the initial pH of the solution be kept in the range 7.5±0.5 and most preferably in the range of 7.2±0.2 by using a suitable reagent selected from the group consisting of acetic acid, citric acid, boric acid, ethylenediaminetetraacetic acid, hydrochloric acid, sulfuric acid, triethyl amine, diisopropylamine, pyridine, sodium bicarbonate, potassium bicarbonate, sodium carbonate, potassium carbonate, calcium carbonate, calcium hydroxide, magnesium hydroxide, magnesium oxide or its suitable combination thereof. The selection of the amount of this suitable reagent can be chosen in a manner so that final pH after completion of reaction does not exceed 8.5.

In another embodiment of the present invention wherein the conversion of racemic alkyl 3-cyano-5-methyl-hexanoate of formula (VII) to substantially enantiopure (S)-ester (VIII) in step (f), the pH of the reaction mixture during the progress of the reaction preferably can be allowed to increase slowly in the range of 7 to 9 while most preferably the pH can be allowed to increase up to ≥7.5 to ≤8.5.

In another embodiment of the present invention wherein the conversion of racemic alkyl 3-cyano-5-methyl-hexanoate of formula (VII) to substantially enantiopure (S)-ester (VIII) in step (f), the enzymatic step can optionally be carried out in presence of salts which can be selected from the group consisting of lithium chloride, sodium chloride, potassium chloride, calcium chloride, magnesium chloride and the like or can be generated in situ by neutralization of suitable acid and a suitable base.

In another embodiment of the present invention wherein the enzymatic step (f) preferably carried out at a temperature range between 20° C. to 45° C., more preferably 22° C. to 40° C. and the most preferably a temperature range between 25° C. to 35° C.

In another embodiment of the present invention wherein the said organic solvent in step (g) is preferably selected from the group consisting of water, methyl alcohol, ethyl alcohol, isopropyl alcohol, n-propyl alcohol, n-butyl alcohol, isobutyl alcohol, tertiary butyl alcohol, cyclohexanol, toluene, monochlorobenzene, dichlorobenzene, tetra hydrofuran, 2-methyl tetra hydrofuran, 1,4-dioxane, dimethylformamide, dimethyl amine, dimethyl sulfoxide, sulfolane and the like.

In an embodiment of the present invention wherein the said base used in step (g) is preferably selected from the group consisting of triethyl amine, diisipropylethyl amine, pyridine, piperidine, 1,8-diazabicyclo[5.4.0]undec-7-ene, 1,4-diazabicyclo[2.2.2]octane, sodium bicarbonate, potassium bicarbonate, sodium carbonate, potassium carbonate, alkali and alkaline earth metal, $C_1$-$C_6$ alkoxide and the like.

In another embodiment of the present invention wherein the said enzymatic step (g) preferably carried out at a temperature range between 25° C. to 200° C. for 1 to 60 hours, more preferably 50° C. to 180° C. for 2 to 24 hours.

In another embodiment of the present invention wherein the base for hydrolysis in step (h) is selected from alkali or alkaline earth metal hydroxides selected from lithium hydroxide, sodium hydroxide, potassium hydroxide, calcium hydroxide, magnesium hydroxide, barium hydroxide, $C_1$-$C_5$ quaternary ammonium hydroxide and the like.

In another embodiment of the present invention wherein the step (h) the said preparation of pregabalin of formula (I) comprises in-situ hydrolysis of compound of structure (VIII) followed by catalytic hydrogenation while the base strength for hydrolysis can be selected from 0.1N to 5N; more preferably from 0.3 to 3N and most preferably from 0.5N to 2N.

In another embodiment of the present invention wherein the said organic solvent in step (h) is selected from the group consisting of water, methyl alcohol, ethyl alcohol, isopropyl alcohol, n-propyl alcohol, n-butyl alcohol, isobutyl alcohol, tertiary butyl alcohol, cyclohexanol, toluene, monochlorobenzene, dichlorobenzene, tetra hydrofuran, dioxane, dimethylformamide or a combination thereof.

In another embodiment of the present invention wherein the said suitable hydrogenation catalyst is preferably selected from the group consisting of nickel, palladium, ruthenium, rhodium with or without support and their different chemical forms and grades optionally fresh or recovered or mixture of fresh and recovered catalyst while the most preferred catalyst is Nickel and palladium.

In another embodiment of the present invention wherein the step (h) preferably carried out at a temperature range between 10° C. to 100° C., more preferably 15° C. to 60° C. and the most preferably a temperature range between 25° C. to 50° C.

In another embodiment of the present invention wherein catalytic hydrogenation in the step (h) is preferably carried out with the hydrogen pressure in the range of 0.5 to 25 kg/cm$^2$ or equivalent unit; whilst the preferable hydrogen pressure in the range of 2 to 15 kg/cm$^2$ or equivalent units and most preferred pressure range is 3 to 10 kg/cm$^2$.

In yet another embodiment of the present invention for the preparation of pregabalin of formula (I) comprise optional charcoalization of hydrogenation product and isolation of pregabalin by preferably isoelectric focusing in the pH range of 6.9 to 7.3, more preferably at pH 7 to 7.2 and crystallization of crude from water, $C_1$-$C_5$ alcohol or a mixture thereof.

In yet another embodiment of the present invention for the preparation of pregabalin of formula (I) comprise isolation of pregabalin by isoelectric focusing wherein the pH can be adjusted with any inorganic or organic acid such as hydrochloric acid, sulfuric acid, acetic acid, phosphoric acid, formic acid, trifluoroacetic acid and the like while the most preferred acid is hydrochloric acid or acetic acid.

In yet another embodiment of the present invention for the preparation of pregabalin of formula (I) comprises purification of pregabalin by crystallization of crude from water, $C_1$—$O_5$ alcohol or a mixture thereof and recovering further amount of pure pregabalin of formula (I) by recrystallization of dried mother liquor.

In still another embodiment of the present invention for the preparation of pregabalin of formula (I) further comprises alternative recovery of pregabalin of formula (I) from the mother liquor preferably as an amino protecting derivative such as tert-butyloxycarbonyl, carboxybenzyl, trityl and the like known in the art, more preferably tert-butyloxycarbonyl can be used and subsequent removal of tert-butyloxycarbonyl group by treatment with acid in a suitable solvent.

EXAMPLES

The invention is further illustrated by the following examples, which should not be construed to limit the scope of the invention in anyway.

Example 1.1: Preparation of
2-cyano-5-methyl-hex-2-enoic acid methyl ester

In a 3 liter four necked RBF, equipped with mechanical stirrer, Dean-Stark condenser methyl cyano acetate (300.0 g), isovaleraldehyde (273 g; 1.05 equiv.) and cyclohexane (210 ml; 0.7 V) were added at room temperature under stirring followed by addition of piperidine (2.7 g; 0.01 equiv.) in cyclohexane (90 ml; 0.3 V through addition funnel. Exothermic reaction was observed (temperature rises from 22° C. to 58° C.). The reaction mixture was refluxed and water was collected azeotropically from Dean-Stark (55 ml) during 2 hrs. After completion of reaction, arrange the distillation set up and distilled out 260 ml of cyclohexane from RM by applying line vacuum at 50° C. The reaction mixture was allowed to cool at 30° C. to get the desired compound 515 gm (>100% of theoretical yield) with purity of 95.90% by GC and this material was used as such for subsequent step. $^1$H-NMR (CDCl$_3$, 400 MHz): 0.98 (d, 6H), 1.92 (m, 1H), 2.45 (t, 2H), 3.88 (s, 3H), 7.68 (t, 1H).

Example 1.2: Preparation of
2-cyano-5-methyl-hex-2-enoic acid methyl ester

In a 3 liter four necked RBF, equipped with mechanical stirrer, Dean-Stark condenser methyl cyano acetate (300.0 g), isovaleraldehyde (273 g; 1.05 equiv.) and cyclohexane (210 ml; 0.7 V) were added at room temperature under stirring followed by addition of piperidine (2.7 g; 0.01 equiv.) in cyclohexane (90 ml; 0.3 V through addition funnel. Exothermic reaction was observed (temperature rises from 22° C. to 58° C.). The reaction mixture was refluxed and water was collected azeotropically from Dean-Stark (55 ml) during 3.5 hrs. d 510 gm (100.8% of theoretical yield) with purity of 93.76% by GC and this material was purified by distillation under vacuum to give desired compound 414.78 g (81.33%; purity by GC 97.2%) and another enriched fraction of 53.7 g (10.53%; GC purity 90.03%) which can be recycled for subsequent batch.

Example 1.3: Preparation of
2-cyano-5-methyl-hex-2-enoic acid methyl ester

In a 100 ml two necked RBF, equipped with mechanical stirrer and addition funnel methyl cyano acetate (5.0 g), isovaleraldehyde (4.35 g; 1.0 equiv.) and cyclohexane (3.5 ml; 0.7 V) were added at room temperature under stirring followed by addition of piperidine (0.043 g; 0.01 equiv.) in cyclohexane (1.5 ml; 0.3 V through addition funnel. Exothermic reaction was observed (temperature rises from 22° C. to 58° C.). The reaction mixture was stirred at ambient temperature (25-30° C. for 3 h. After completion of reaction, the reaction mixture was washed with water. It was optionally dried over anhydrous $Na_2SO_4$. Solvent was removed by distillation and the residue was dried under vacuum to get the desired compound 510 gm (100.8% of theoretical yield) with purity of 93.76% by GC and this material was purified by distillation under vacuum to give 8.5 g (>100%; purity by GC 91.5).

Example 2.1: Preparation of
2-isobutylsuccinonitrile (V)

In a 2 lit. four necked RBF equipped with mechanical stirrer, thermometer pocket, Dean-Stark condenser over oil bath, 2-cyano-5-methyl-hex-2-enoic acid methyl ester (200.0 g; GC purity 97.2%) was placed followed by the addition of water (200 ml; 1.0 V). To the resulting milky reaction mixture a solution of sodium cyanide (58.61 g; 1.0 equiv.) in water (400 ml; 2.0 V) was added drop wise for 15 min. During the addition rise in temperature from 22 to 41° C. was observed. After the addition was over the reaction mixture was heated at 92° C. for 3 hr. The reaction mixture was cooled to 30° C. The organic layer was removed and washed with water (200 ml). Weight of compound V was 96.0 g with 96.08% purity by GC. The aqueous layers were combined and again heated at 92° C. for 4 hr. It was extracted with MTBE. The organic layer was separated from the aqueous layer and washed with 200 ml of water (1.0 V). Weight of compound V was 20.0 g ($2^{nd}$ crop; with purity of 97.14% by GC. Combined the aqueous layers and extracted with MTBE (400 ml). Separate organic layer and dried over sodium sulphate. The solvent was distilled. Weight of compound V was 19.0 g. ($3^{rd}$ crop; with purity of 91.5% by GC. Total crude wt. of compound V was 135 g (Yield, 82.87%). $^1$H-NMR (CDCl$_3$, 400 MHz): 2.981 (1H, m), 2.712 (2H, d), 1.875 (1H, m), 1.816 (1H, m), 1.530 (1H, m), 1.016 (314, d), 0.981 (3H, d).

Example 2.2

In a 1 liter round bottom flask, 2-cyano-5-methyl-hex-2-enoic acid methyl ester (100 g) obtained in example 1.1 was dissolved in MeOH (200 ml, 2V) and a solution of sodium cyanide (29.3 g; 1.0 equiv.) in water (100 ml; 1 V) was added drop wise for ~1 h; an exotherm observed up to 42° C. After the addition was over, downward distillation was set up and distilled out methanol from reaction mass till the reaction mass temperature reaches to 95° C. Continue heating at ~95° C. for 3 hr. Solid started to fall out after methanol distillation. The reaction mixture was cooled to 30° C. Suspension of solid material was observed. Water (150 ml; 1.5 V) was added to break the suspension to obtain two clear layers. The organic layer was separated from the aqueous layer and washed with water (100 ml). Weight of compound V was 64 g (yield, 78.5%; purity 94.86% by GC).

Example 2.3

In a 3 liter round bottom flask, 2-cyano-5-methyl-hex-2-enoic acid methyl ester (515 g) obtained in example 1.1 was dissolved in MeOH (420 ml) and a solution of sodium cyanide (147 g; 1.0 equiv.) in water (630 ml; 2.1 V) was added drop wise for ~30 min; an exotherm observed up to 45-50° C. After the addition was over, downward distillation was set up and distilled out methanol from reaction mass till the reaction mass temperature reaches to 95° C. Continue heating at ~95° C. for 1 hr. Solid started to fall out after methanol distillation. The reaction mixture was cooled to 30° C. Suspension of solid material was observed. Water (500 ml; 1.6 V) was added to break the suspension to obtain two clear layers. The organic layer was separated from the aqueous layer and washed with water (300 ml). Weight of compound V was 389.7 g ($1^{st}$ crop) The aqueous layers were combined together and extracted with MTBE (500 ml). The MTBE layer was separated and optionally dried over anhydrous $Na_2SO_4$. After distillation of MTBE 9.0 g. ($2^{nd}$ crop) of compound V was obtained. Total crude wt. of compound V is 401 g (yield, 97.24%; purity 92.1% by GC). The crude was further purified by distillation to obtain at 100-104° C./2.0-2.5 torr to obtain 338 g (82%) of pure product with >98% GC purity another ~8-10% impure fractions were collected with purity of ~90% and can be recycled for subsequent distillation.

Example 2.4

In a 2 liter round bottom flask, 2-cyano-5-methyl-hex-2-enoic acid methyl ester (100 g) as obtained in example 1.1 was stirred with water (100 ml; 1 V) and a solution of sodium cyanide (29.4 g; 1.0 equiv.) in water (200 ml; 2 V) was added drop wise for ~15 min; an exotherm observed up to 30° C. After the addition was over, reflux the reaction mixture at 89-92° C. for 10 hrs. The reaction mixture was cooled to 30° C. The organic layer was separated from the aqueous layer and washed with water (100 ml). Weight of compound V was 68.5 g ($1^{st}$ crop) The aqueous layers were combined together and extracted with MTBE (200 ml). The MTBE layer was separated and optionally dried over anhydrous $Na_2SO_4$. After distillation of MTBE 2.5 g. ($2^{nd}$ crop) of compound V was obtained. Total crude wt. of compound V is 70 g (yield, 87.12%; purity 96.88% by GC).

Example 2.5

Arranged the reaction set up consist of 500 ml four neck RBF, mechanical stirrer and thermometer pocket over an oil bath. Methyl cyanoacetate 50 g (0.505 mol) and isovaleraldehyde 43.4 g (0.505 mol) were dissolved in MeOH (50 ml). A solution of sodium cyanide (24.52 g; 0.505 mol) of sodium cyanide in 80 ml water was added slowly under stirring (exotherm observed up to ~25-54° C.). Additional water (20 ml) was used to rinse the dropping funnel. The reaction mixture was heated at 74-76° C. (reflux temperature) and maintained for 3.0 hrs. After removing reflux condenser downward distillation assembly was fitted and started down ward distillation to remove methanol from the reaction mass till the temperature of the reaction mass reached 95° C. The reaction mixture was maintained at this temperature for 5.0 hrs The reaction mixture was slowly cooled to room temperature. The upper oily layer of the product was separated and washed with water (50 ml×2). Weight of the oil was 58.0 g (yields 84.40%; purity 98.63% by GC). All the aqueous layers were pulled together and extracted with MTBE (50 ml×2). The organic layer was dried over sodium sulphate and evaporated at 40° C. under vacuum to give a second crop of 3.0 g (yield 4.36%; 96.32% by GC). The combined yield was 88%.

Example 2.6

Arranged the reaction set up consist of 1000 ml four neck RBF, mechanical stirrer and thermometer pocket over an oil bath. Methyl cyanoacetate (100.0 g) and isovaleraldehyde (86.92 g) were added to 100 ml water. A solution of sodium cyanide (49.5 g; 1.0 equiv.) in water (200 ml) was added drop wise to the above mixture under stirring for 30 min. A down ward distillation assembly was set up and started distilling out methanol from reaction mass till temperature of the reaction mass reached to >90° C. Maintain the reaction mass temperature in range of 90-98° C. for further 12 hrs. The reaction mixture was cooled to 30° C. The organic layer was separated from the aqueous layer and washed the organic layer with 200 ml of water. Weight of compound V was 130 g (yield 94.0%; purity 95.81% by GC analysis)

Example 2.7

In a 2 L four neck RBF, equipped with mechanical stirrer and thermometer pocket over oil bath, methyl cyanoacetate (200 g; 1 eqv) and isovaleraldehyde (173.84 g; 1.0 eqv) were dissolved in 200 ml (1.0 V) MeOH at 25° C. A solution of sodium cyanide (98.90 g; 1.0 eqv.) in 400 ml water (2.0 V) was added drop wise at 25° C. over 1.5 h. The reaction mass was heated at 80° C. for 3 h and checked the consumption of methyl cyanoacetate by GC. A downward distillation assembly was attached and distilled out methanol from the reaction mass till reaction mass temperature reached to 92° C. during the period of 3 h. Then reaction mass becomes solid. To avoid solidification, 200 ml (1V) of water was added. The reaction mixture was maintained between 92-94° C. for further 5 h. The organic layer formed was separated from the aqueous layer. The organic layer was washed with 200 ml of water (1.0 V). Weight of compound V was 240 g (87.30% yields) with GC purity 96.89%. The aqueous layer was extracted using MTBE (2×200 ml). The MTBE layer was dried over anhydrous sodium sulphate. Distillation of MTBE under reduced pressure at 45° C. gave 5.3 g of product V with GC purity: 75.0%]). The crude compound V (245.3 g) was purified by distillation under high vacuum to get 234.2 g (85.2%) purified compound V with 99.26% purity by GC.

Example 3.1: Preparation of racemic 3-cyano-5-methyl-hexanoic acid (VI)

A one liter four necked RBF was equipped with mechanical stirrer, thermometer pocket and a pH meter probe. Crude compound V (50.0 g) and 666 ml of water (13.3 V) were added in the flask at rt (25° C.). The pH of the solution was adjusted at 7.5±0.2 using solid $NaHCO_3$. The reaction mixture was warmed to 30° C. and Nitrilase enzyme preparation (4.0 ml; sp. activity 230 U/ml) was added to the reaction mixture. The reaction mixture was stirred at 30° C. for 24 hrs by keeping the pH at ~7.5. After 24 hrs, the reaction mixture was brought to 25° C. The reaction mass was extracted with MTBE (150 ml) and after evaporator at 45° C. under 150 Torr gave a recovery of 0.5 g un-reacted starting material. The aq. layer was acidified to pH 1.0 by addition of conc. HCl (~50 ml). The aqueous layer was extracted with MTBE (2×150 ml). The combined MTBE layer optionally dried over sodium sulphate. Evaporation of MTBE layer gave 54 g (94.78% yield; purity 94.40% by GC) of compound VI ($R_2$=H). $^1$H-NMR ($CDCl_3$, 400 MHz): 3.048 (1H, m), 2.768 (1H, dd), 2.615 (1H, dd), 1.883 (1H, m), 1.674 (1H, m), 1.368 (1H, m), 0.998 (3H, d), 0.978 (3H, d).

Example 3.2

In a 5 L four necked RBF, equipped with mechanical stirrer, thermometer pocket and pH meter, compound V (200.0 g; 1.0 eq) and 2660 ml of water were taken at 25° C. The pH was adjusted at 7.5±0.2 using solid $NaHCO_3$. The reaction mixture was warmed to 35°±2° C. and Nitrilase enzyme (16.0 ml; sp activity 230 U/ml) was added to the reaction mixture. The reaction mixture was stirred at 35°±2° C. for 24 h by maintaining the pH at 7.5±0.2 (if required adjust the pH by using solid $NaHCO_3$ or 1N HCl). The reaction was monitored by GC after 23 h (unreacted compound III ≤1%). The reaction mixture was cooled to 25° C. and filtered the reaction mass. The reaction mass was extracted with MTBE (2×300 ml) and concentrate under reduced pressure at 45° C. to recover un-reacted starting material (1.0 g). The aqueous layer was acidified to pH 1-2 by adding conc. HCl (200 ml). The aqueous layer was extracted with MTBE (3×400 ml). The MTBE layer was dried over sodium sulphate. Distillation of MTBE layer under reduced pressure at 45° C. gave 218.1 g (95.69%) of compound VI ($R_2$=H) with purity of 91.07% by GC.

Example 3.3

In a 250 ml four necked RBF, equipped with mechanical stirrer, thermometer pocket and pH meter, compound V (10.0 g; 1.0 eq), 100 ml of water (10 V) and 5 ml MeOH (0.5 V) were taken at 30° C. The pH was adjusted at 7.5±0.2 using solid $NaHCO_3$. The reaction mixture was maintained at 30° C. and Nitrilase enzyme (0.76 ml; sp activity 300 U/ml) was added to the reaction mixture. The reaction mixture was stirred at 30° C. for 24 h by maintaining the pH at 7.5±0.2 (if required adjust the pH by using solid $NaHCO_3$ or 1N HCl). The reaction was monitored by GC after 23 h (unreacted compound V≤1%). The reaction mixture was cooled to 25° C. and filtered the reaction mass. The reaction mass was extracted with MTBE (2×25 ml) and concentrate under reduced pressure at 45° C. to recover un-reacted starting material (3.9 g). The aqueous layer was acidified to pH 1-2 by adding conc. HCl. The aqueous layer was extracted with MTBE (2×40 ml). The MTBE layer was dried over sodium sulphate. Distillation of MTBE layer under reduced pressure at 45° C. gave 6.5 g (57.52%) of compound VI ($R_2$=H) with purity of 77.82% by GC.

Example 3.4

In a 250 ml four necked RBF, equipped with mechanical stirrer, thermometer pocket and pH meter, compound V (10.0 g; 1.0 eq), 50 ml of water (5 V) were taken at 30° C. The pH was adjusted at 7.5±0.2 using solid NaHCO$_3$. The reaction mixture was maintained at 30° C. and Nitrilase enzyme (0.76 ml; sp activity 300 U/ml) was added to the reaction mixture. The reaction mixture was stirred at 30° C. for 24 h by maintaining the pH at 7.5±0.2 (if required adjust the pH by using solid NaHCO$_3$ or 1N HCl). The reaction was monitored by GC after 23 h (unreacted compound V≤1%). The reaction mixture was cooled to 25° C. and filtered the reaction mass. The reaction mass was extracted with MTBE (2×25 ml). The aqueous layer was acidified to pH 1-2 by adding conc. HCl. The aqueous layer was extracted with MTBE (2×40 ml). The MTBE layer was dried over sodium sulphate. Distillation of MTBE layer under reduced pressure at 45° C. gave 3.8 g (33.62%) of compound VI (R$_2$=H) with purity of 75.12% by GC.

Example 3.5

In a 500 ml four necked RBF, equipped with mechanical stirrer, thermometer pocket and pH meter, compound V (25.0 g; 1.0 eq), 332.5 ml of water (13.3 V) were taken at 30° C. The pH was adjusted at 7.5±0.2 using solid NaHCO$_3$ (1.17 g). The reaction mixture was maintained at 30° C. and Nitrilase enzyme (2.7 ml; sp activity 300 Um') was added to the reaction mixture. The reaction mixture was stirred at 30° C. for 24 h by maintaining the pH at 7.5±0.2 (if required adjust the pH by using solid NaHCO$_3$ or 1N HCl). The reaction was monitored by GC after 23 h (unreacted compound V≤1%). The reaction mixture was cooled to 25° C. and filtered the reaction mass. The reaction mass was extracted with MTBE (2×25 ml). The aqueous layer was acidified to pH 1-2 by adding conc.HCl. The aqueous layer was extracted with MTBE (2×40 ml). The MTBE layer was dried over sodium sulphate. Distillation of MTBE layer under reduced pressure at 45° C. gave 25.6 g (89.98%) of compound VI (R$_2$=H) with purity of 78.3% by GC.

Example 3.6

In a 500 ml four necked RBF, equipped with mechanical stirrer, thermometer pocket and pH meter, compound V (25.0 g; 1.0 eq), 332.5 ml of water (13.3 V) were taken at 30° C. The pH was adjusted at 7.5±0.2 using solid NaHCO$_3$ (1.17 g). The reaction mixture was maintained at 30° C. and Nitrilase enzyme (3.37 ml; sp activity 300 U/ml) was added to the reaction mixture. The reaction mixture was stirred at 30° C. for 24 h by maintaining the pH at 7.5±0.2 (if required adjust the pH by using solid NaHCO$_3$ or 1N HCl). The reaction was monitored by GC after 23 h (unreacted compound V≤1%). The reaction mixture was cooled to 25° C. and filtered the reaction mass. The reaction mass was extracted with MTBE (2×25 ml). The aqueous layer was acidified to pH 1-2 by adding cone. HCl. The aqueous layer was extracted with MTBE (2×40 ml). The MTBE layer was dried over sodium sulphate. Distillation of MTBE layer under reduced pressure at 45° C. gave 26.6 g (93.75%) of compound VI (R$_2$=H) with purity of 84.73% by GC.

Example 3.7

In a 500 ml four necked RBF, equipped with mechanical stirrer, thermometer pocket and pH meter, compound V (25.0 g; 1.0 eq), 250 ml of water (10 V) and 1.25 ml MeOH were taken at 35° C. The pH was adjusted at 7.5±0.2 using solid NaHCO$_3$ (1.75 g). The reaction mixture was maintained at 35° C. and powdered Nitrilase enzyme (1.75 g; sp activity 300 U/ml; 16.2 u/g) was added to the reaction mixture. The reaction mixture was stirred at 35° C. for 24 h by maintaining the pH at 7.5±0.2 (if required adjust the pH by using solid NaHCO$_3$ or 1N HCl). The reaction was monitored by GC after 24 h (unreacted compound V≤1%). The reaction mixture was cooled to 25° C. and filtered the reaction mass. The reaction mass was extracted with MTBE (2×25 ml). The MTBE layer was evaporated to recover 4.5 g (18%) compound V. The aqueous layer was acidified to pH 1-2 by adding conc. HCl. The aqueous layer was extracted with MTBE (2×40 ml). The MTBE layer was dried over sodium sulphate. Distillation of MTBE layer under reduced pressure at 45° C. gave 20.5 g (71.92%) of compound VI (R$_2$=H) with purity of 97.82% by GC.

Example 3.8

In a 30 lit reactor charged 9.0 kg of water at 25° C. to 35° C. In a clean HDPE container charged 10.99 lit of water and 1.500 kg (1.0 eq) of compound V at 25° C. to 35° C. and micronized for 30 min. After micronization formation of fine globules observed and was transferred to the reactor. The pH of the mixture was adjusted to 7.5±0.2 using solid NaHCO$_3$ (~30.0 gm). The temperature of the reaction mass was brought to 35±2° C. and charged nitrilase enzyme 129.26 gm (sp. activity: 0.235 kU/mL) in one portion. The container of the enzyme was rinsed with 0.2 V water and charged to reactor. The pH of reaction mass was adjusted to 7.5±0.2 by using solid NaHCO$_3$. The reaction mixture was stirred at 35±2° C. for 14.0 h by maintaining the pH 7.5±0.2 by adding sodium bicarbonate solution or with dilute hydrochloric acid. Continue the reaction till compound V <1%. Filter the reaction mass from reactor by using Buchner filter under vacuum. Charge filtrate to reactor and adjust pH to 1-2 by using conc. hydrochloric acid and (~1.56 kg). The filtrate was extracted with MTBE (3×3.0 lit). Concentrated the MTBE layer under reduced pressure at 45° C. and vacuum 400-10 for to give compound VI in 90.3% assay based yield.

Example 4.1: Preparation of methyl 3-cyano-5-methyl-hexanoate

Arranged a 100 ml single neck RBF, equip with magnetic needle with a reflux condenser fitted with a guard tube on magnetic stirrer. Racemic 3-cyano-5-methyl-hexanoic acid (5 g) was dissolved in MeOH (50 ml; 10.0 V) and cooled to 0-5° C. followed by addition of thionyl chloride (4.59 g; 1.2 eqv.) drop wise at room temperature. The resulting solution was stirred at room temperature for 16 hrs. After evaporation of the reaction mass under vacuum the oily residue was diluted with water (25 ml) and extracted with ethyl acetate (15×3 ml). The organic layer was washed with saturated bicarbonate solution (5 ml×3) and brine (5 ml). It was optionally dried over anhydrous sodium sulphate and concentrated to get 3.8 g (yield 69.7%~85% by GC). $^1$H-NMR (CDCl$_3$, 400 MHz): 3.746 (3H), 3.082 (1H, m), 2.723 (1H, dd), 2.571 (1H, dd), 1.882 (1H, m), 1.655 (1H, m), 1.352 (1H, m), 0.974 (3H, d), 0.958 (3H, d).

Example 4.2: Preparation of methyl 3-cyano-5-methyl-hexanoate

Arranged a 250 ml single neck RBF, equip with magnetic needle and a reflux condenser fitted with a guard tube on magnetic stirrer. Racemic 3-cyano-5-methyl-hexanoic acid (9.0 g) was added in MeOH (90 ml; 10.0 V) and cooled to 0-5° C. followed by addition of trimethylsilyl chloride (6.29 g; 1.0 eqv.) drop wise at 0-5° C. for 5 minutes. The resulting solution was stirred at room temperature for 48 hrs. After evaporation of the reaction mass under vacuum the oily residue was diluted with water (50 ml) and extracted with ethyl acetate (20×3 ml). The organic layer was washed with saturated bicarbonate solution (5 ml×3) and brine (5 ml). It was optionally dried over anhydrous sodium sulphate and concentrated to get 9 g (yield 91.7% and purity of 97.2% by GC) of compound VII ($R_3$=methyl).

Example 4.3: Preparation of methyl 3-cyano-5-methyl-hexanoate

Arranged a 2 L single neck RBF, equipped with magnetic needle with reflux condenser fitted with a guard tube on magnetic stirrer. Racemic 3-cyano-5-methyl-hexanoic acid (150 g) was added in MeOH (750 ml;) followed by 12 g $H_2SO_4$ (0.12 eq.) at 25° C. Stir the reaction mass for 1 h at reflux temperature (68° C.). After evaporation of the reaction mass under vacuum the oily residue was diluted with water (750 ml) and extracted with ethyl acetate (150×3 ml). The organic layer was washed with saturated bicarbonate solution (100 ml×2). It was optionally dried over anhydrous sodium sulphate and concentrated to get 155.5 g (yield 95% purity >96% by GC) of compound VII ($R_3$=methyl).

Example 4.4: Preparation of methyl 3-cyano-5-methyl-hexanoate

Arranged a 2 L two neck RBF, equipped with overhead stirrer and reflux condenser fitted with a guard tube. Racemic 3-cyano-5-methyl-hexanoic acid (443 g) was dissolved in MeOH (2215 ml; 5.0 V) followed by $H_2SO_4$ (35.44 g; 0.12 eq.) at 25° C. Stir the reaction mass for 1 h at reflux temperature (68° C.). After evaporation of the reaction mass under vacuum the oily residue was diluted with water (2000 ml) and extracted with ethyl acetate (300×3 ml). The organic layer was washed with by saturated bicarbonate solution (100 ml×2). It was optionally dried over anhydrous sodium sulphate and concentrated to get 459.1 g (yield 95%; purity >97.62% by GC) of compound V ($R_3$=methyl). This material was distilled under vacuum to get compound VII in 85.52% yield with GC assay >99.5%.

Example 4.5: Preparation of methyl 3-cyano-5-methyl-hexanoate

Arranged a 2 L two neck RBF, equipped with overhead stirrer and reflux condenser fitted with a guard tube. Racemic 3-cyano-5-methyl-hexanoic acid (410 g) was dissolved in MeOH (2050 ml;) followed by $H_2SO_4$ (32.8 g; 0.12 eq.) at 25° C. Stir the reaction mass for 1 h at reflux temperature (68° C.). After evaporation of the reaction mass under vacuum the oily residue was diluted with water (2000 ml) and extracted with toluene (300 ml×3). The organic layer was washed with water (300 ml) followed by saturated bicarbonate solution (100 ml×2). It was optionally dried over anhydrous sodium sulphate and concentrated to get 425.6 g (yield 95.2%; purity >95.59% by GC) of compound V ($R_3$=methyl). This material was further purified by distillation under vacuum to get compound VII in 86.18% yield with GC assay >99.8%.

Example 4.6: Preparation of methyl 3-cyano-5-methyl-hexanoate

In a clean and dry 30 lit reactor charged MeOH (5.43 lit) at 25-30° C. and racemic 3-cyano-5-methyl-hexanoic acid (1.81 kg) under stirring. The cyano acid container was rinsed with MeOH (1.81 lit) and transfer into the reactor followed by $H_2SO_4$ (0.145 kg; 8% wrt cyano acid) at 25-30° C. Stir the reaction mass for 1 h at reflux temperature (65-68° C.). After evaporation of the reaction mass under vacuum the oily residue was diluted with water (9.05 lit) and extracted with toluene (1.81 lit×3 ml). The combined organic layer was washed with saturated bicarbonate solution (1.81 lit×2). It was distilled to remove toluene 40-45° C. get 425.6 g (yield 95.2%; purity >95.59% by GC) of compound VII ($R_3$=methyl). This material was further purified by distillation using thin film evaporator to get compound VII in 79.18% yield based on purity with GC assay >96.14%.

Example 4.7: Preparation of methyl 3-cyano-5-methyl-hexanoate starting from methyl cyanoacetate In a 1 L four neck RBF, equipped with mechanical stirrer and thermometer pocket over oil bath, methyl cyanoacetate (100 g; 1 eqv) and isovaleraldehyde (95.6 g; 1.0 eqv) were dissolved in 100 ml (1.0 V) methanol at 25° C. A solution of sodium cyanide (98.90 g; 1.0 eqv.) in 200 ml water (2.0 V) was added drop wise at 25° C. over 1.5 h. The reaction mass was heated at 80° C. for 3 h and checked the consumption of methyl cyanoacetate by GC. Additional water (100 ml) was added. A downward distillation assembly was attached and distilled out methanol from the reaction mass till reaction mass temperature reached to 92° C. during the period of 3 h. The reaction mixture was maintained between 92-94° C. for further 5 h. The organic layer formed was separated from the aqueous layer. The organic layer was washed with 200 ml of water (1.0 V). Weight of compound V was 128 g (93.12% yields) with GC purity 95.82%.

A one liter four necked RBF was equipped with mechanical stirrer, thermometer pocket and a pH meter probe. Crude compound V obtained above (25.0 g, 95.82% purity) and 333 ml of DM water (13.3 V) were added in the flask at 25° C. The pH of the solution was adjusted at 7.5±0.2 using solid $NaHCO_3$ (~2.0 g was required). The reaction mixture was warmed to 30° C. and Nitrilase enzyme preparation (1.8 ml; 20.5 u/g substrate; sp. activity 257 U/ml) was added to the reaction mixture. The reaction mixture was stirred at 35° C. for 24 hrs by keeping the pH at 7.5±0.2 (by using solid $NaHCO_3$ or 1N HCl as and when required). After 24 hrs, the reaction mixture was brought to 25° C. The reaction mass was extracted with MTBE (75 ml) and after evaporator at 45° C. under 150 Torr gave a recovery of 0.25 g un-reacted starting material. The aq. layer was acidified to pH 1.0 by addition of conc. HCl (~50 ml). The aqueous layer was extracted with MTBE (2×75 ml). The combined MTBE layer optionally dried over sodium sulphate. Evaporation of MTBE layer gave 24.5 g (86% yield; purity 80% by GC) of compound VI ($R_2$=H).

Arranged a 250 ml single neck RBF, equipped with magnetic needle with reflux condenser fitted with a guard tube on magnetic stirrer. Racemic 3-cyano-5-methyl-hexanoic acid (24 g) as obtained above was added in MeOH (72 ml; 3.0 V) followed by 2.4 g $H_2SO_4$ at 25° C. Stir the reaction mass for 1 h at reflux temperature (64-65° C.). After evaporation of the reaction mass under vacuum the oily residue was diluted with water (375 ml) and extracted with ethyl acetate (50 ml×3). The organic layer was washed with saturated bicarbonate solution (20 ml×2). It was optionally dried over anhydrous sodium sulphate and concentrated to get 24 g (yield 91.7%; purity >93.4% by GC) of compound VII ($R_3$=methyl).

Preparation of methyl 3-cyano-5-methyl-hexanoate by Recycling R Enriched Acid through Racemization

TABLE 1 optimization of racemization of R enriched acid.

| Sr No. | Batch Size g (eq.) Purity Chiral HPLC purity (R:S) | Base g (eq.) | Solvent (V) | Temp/ Time (° C./h) | Remark Yield (g/%) purity Chiral HPLC/GC Purity |
|---|---|---|---|---|---|
| 1 | 1.0/(1) 96.16 94.74:5.26 | KO$^t$Bu, 0.66 (1) | DMSO | 130/5 | 59.37, acid, (11.60) 48.87:51.12 |
| 2 | 1.0/(1) 81.69 85.11:14.88 | KO$^t$Bu, 1.45 (2) | DMSO (10) | 27/24 | 72.3, acid, (11.60) 59.16:40.83 |
| 3 | 1.0/(1) 81.69 85.11:14.88 | NaHCO$_3$, 0.55 (1); KO$^t$Bu, 0.73 (1) | DMSO (10) | 27/48 | 69.48:30.31 |
| 4 | 5.0/(1) 81.69 85.11:14.88 | KOH, 3.60 (2) | MeOH (50) | 65/120 | 66.32, acid, (11.69) 57.94:42.05 |
| 5 | 1.0/(1) 81.69 85.11:14.88 | K$_2$CO$_3$ 0.52 (2) | MeOH (10) | 65/60 | 69.45:30.54 |
| 6 | 0.2/(1) 86.05:13.94 | NaOMe 0.139 (2.0) | Toluene | 110/18 | 0.147/73.5 89.21:10.78 |
| 7 | 1.0/(1) 81.69 85.11:14.88 | KOH 0.72 (2) | Acetone 10 | 56/60 | 53.25:46.74 |
| 8 | 1.0/(1) 81.69 85.11:14.88 | NaOH 0.52 (2) | MeOH 10 | 65/15 | 75.33:24.6 |
| 9 | 1.0/(1) 81.69 85.11:14.88 | NaOH 0.52 (2) | n-Butanol 10 | 118/15 | 0.4/40 23.57, acid, (11.59) 53.66:46.33 |
| 10 | 1.0/(1) 81.69 85.11:14.88 | NaOH 0.52 (2) | IPA 10 | 82/24 | 51.28:48.71 21.76, acid, (11.59) |

Racemization of R-acid: The esterification of racemized acid to check the chiral GC purity of corresponding isomers

| 11 | 2.0/(1) 73.34 90.26:9.73 | NaHCO$_3$, 1.08 (1) K$_2$CO$_3$, 0.89 (0.5) | DMSO 20 (10) | 100/1 130/18 | 81.98, V, (10.10) 80.42:19.58 |
| 12 | 2.0/(1) 73.34 90.26:9.73 | K$_2$CO$_3$, 3.56 (2.0) | DMSO 20 (10) | 130/24 | 34.14, V, (10.10) 46.84 ? (12.15) 79.87:20.13 |
| 13 | 2.0/(1) 73.34 90.26:9.73 | NaHCO$_3$ 3.25 (3.0) | DMSO 20 (10) | 130/12 | 84.93, V, (10.17) 76.2:23.78 |
| 14 | 2.0/(1) 73.34 90.26:9.73 | NaHCO$_3$ 3.25 (3.0) | DMSO 20 (10) | 130/24 | 54.98, V, (10.13) 65.03:34.97 |
| 15 | 5.0/(1) 73.34 90.26:9.73 | NaHCO$_3$, 2.71 (1) KO$^t$Bu, 1.45 (0.4) | DMSO 50 (10) | 100/12 130/6 | 86.71, V, (10.14) 77.25:22.75 |
| 16 | 5.0/(1) 73.34 90.26:9.73 | NaHCO$_3$, 2.71 (1) KO$^t$Bu, 2.17 (0.6) | DMSO 50 (10) | 100/12 130/6 | 84.02, V, (10.14) 50.16:49.84 |

Racemization of R-acid: Investigation in presence of KO$^t$Bu as base using different mole ratios.

| Batch No. | Batch Size Comp. VII; g (eq.) GC Purity Chiral HPLC purity | NaHCO$_3$ g (eq.) | Solvent mL (v) | Base g (eq.) | Temp/ Time (° C./h) | Yuield g (%); purity Chiral GC Purity of ester |
|---|---|---|---|---|---|---|
| 17 | 2.0/(1) 73.34 90.26:9.73 | 1.08 (1) | DMSO 20 (10) | KO$^t$Bu 0.290 (0.2) | 30/1 130/5 | 82.92:17.08 |

TABLE 1-continued optimization of racemization of R enriched acid.

| 18 | 2.0/(1)<br>73.34<br>90.26:9.73 | NaHCO₃<br>1.08 (1) | DMSO<br>20 (10) | KO'Bu<br>0.44 (0.3) | 100/12<br>130/12 | 81.15<br>75.35:24.65 |

| Investigation with higher temperature and longer time: | | | | | |
|---|---|---|---|---|---|
| 19 | 2.0/(1)<br>73.34<br>90.26:9.73 | NaHCO₃, 1.08 (1)<br>KO'Bu, 0.44 (0.3) | DMSO<br>20 (10) | 100/12<br>130/12 | 81.15<br>75.35:24.65 |
| 20 | 2.0/(1)<br>73.34<br>90.26:9.73 | NaHCO₃<br>3.25 (3.0) | DMSO<br>20 (10) | 130/24 | 54.98<br>65.03:34.97 |
| 21 | 2.0/(1)<br>73.34<br>90.26:9.73 | NaOEt<br>1.32 (1.5) | DMSO<br>20 (10) | 130/18 | 45.54<br>33.78 ? (12.56)<br>R-ester: 50.71; S-ester: 49.29 |
| 22 | 2.0/(1)<br>73.34<br>90.26:9.73 | NaOEt<br>1.32 (1.5) | DMSO<br>20 (10) | 130/2 | 67.58<br>R-ester: 49.98; S-ester: 50.02 |
| 23 | 2.0/(1)<br>73.34<br>90.26:9.73 | NaOEt<br>1.32 (1.5) | DMSO<br>20 (10) | 75/4 | 87.91<br>R-ester: 51.42; S-ester: 48.58 |
| 24 | 2.0/(1)<br>73.34<br>90.26:9.73 | NaOEt<br>1.32 (1.5) | DMSO<br>10 (5) | 75/4 | 85.09<br>R-ester: 52.58; S-ester: 47.42 |
| 25 | 5.0/(1)<br>73.34<br>90.26:9.73 | NaHCO₃, 2.71 (1)<br>NaOEt, 2.19 (1.0) | EtOH<br>50 (10) | 78/40 | 4.0/73.39<br>69.40<br>R-ester: 50.08; S-ester: 49.92 |
| 26 | 5.0/(1)<br>73.34<br>90.26:9.73 | NaHCO₃, 2.71 (1)<br>NaOEt<br>1.65 (0.75) | EtOH<br>50 (10) | 78/4<br>78/16 | 3.9/71.56<br>73.06<br>R-ester: 50.10; S-ester: 49.90 |
| 27 | 5.0/(1)<br>73.34<br>90.26:9.73 | NaHCO₃, 2.71 (1)<br>NaOEt, 2.2 (1.0) | EtOH<br>50 (10) | 78/4<br>78/4 | 4.19/76.88<br>90.18<br>R-ester: 50.63; S-ester: 49.37 |
| 28 | 20.0/(1)<br>73.34<br>90.26:9.73 | NaHCO₃, 10.82 (1)<br>NaOEt, 8.77 (1.0) | EtOH<br>200 (10) | 78/1<br>78/4.5 | 16.8/77.03<br>90.48<br>R-ester: 61.22; S-ester: 38.78 |
| 29 | 30.0/(1)<br>73.34<br>90.26:9.73 | NaHCO₃, 16.23 (1)<br>NaOEt, 9.86<br>(0.75) | EtOH<br>180 (6) | 78/4<br>78/4.5 | 26.8/81.93<br>86.00<br>R-ester: 51.00; S-ester: 49.00 |

Example 4.8: Preparation of methyl-3-cyano-5-methyl-hexanoate from R Enriched (IX)

Assembled a 250 ml single neck RBF, equipped with magnetic needle, thermometer pocket and reflux condenser over an oil bath. R-Enriched 3-cyano-5-methyl-hexanoic acid (5.0 g; 1.0 eqv.) was dissolved in DMSO (25 ml) and NaHCO₃ (1.08 g; 1.0 eqv) was added at 25° C. The reaction mass was heated for 12 h at 100° C. To the hot solution KO'Bu (2.17 g; 0.6 eqv.) was added and stirred for 6 h at 130° C. the reaction mixture was cooled to 25° C. and water (12.5 ml) was added. It was acidified with 1N HCl solution till pH 1-2 and extracted by ethyl acetate (20 ml×3) The EtOAc layer was washed with water (15 ml×3) and dried over anhydrous sodium sulphate. It was concentrated under reduced pressure at 40° C. to give 3.5 g racemic 3-cyano-5-methyl-hexanoic acid. To the residue MeOH (18 ml) was added followed by H₂SO₄ (0.18 g) at 25° C. The reaction mixture was refluxed for 1 h. The reaction mass was concentrated under vacuum ~45° C. and added water (18 ml). The oily layer was extracted using EtOAc (15 ml×3). Combined organic layer was washed with saturated sodium bicarbonate solution (15 ml×2) The organic layer was dried over anhydrous sodium sulphate and concentrate under reduced pressure at 40° C. to give 75% crude with purity ~80% by GC methyl 3-cyano-5-methyl-hexanoate with chiral GC purity data (%): S:R 50.16:49.84.

Example 4.9: Preparation of methyl-3-cyano-5-methyl-hexanoate from R Enriched (IX)

Assembled a 250 ml three neck RBF, equipped with magnetic needle, thermometer pocket and reflux condenser over an oil bath. R-Enriched 3-cyano-5-methyl-hexanoic acid (2.0 g; 1.0 eqv.) was dissolved in EtOH (20 ml) and NaOEt (1.32 g; 1.5 eqv) was added at 25° C. The reaction mass was refluxed for 4 h at 78° C. The reaction mixture was cooled to 25° C. and water (2.0 ml) was added. It was acidified with 1N HCl solution till pH 1-2 and extracted by MTBE (7 ml×3). The combined MTBE layer was dried over anhydrous sodium sulphate. It was concentrated under reduced pressure at 40° C. to give 1.7 g racemic 3-cyano-5-methyl-hexanoic acid. To the residue MeOH (5 ml) was added followed by H₂SO₄ (0.136 g) at 25° C. The reaction mixture was refluxed for 1 h. The reaction mass was concentrated under vacuum ~45° C. and added water (8.5 ml). The oily layer was extracted using EtOAc (5 ml×3). Combined organic layer was washed with saturated sodium bicarbonate solution (5 ml×2) The organic layer was dried over anhydrous sodium sulphate and concentrate under reduced pressure at 40° C. to give 1.6 g (80.8%) of crude methyl-3-cyano-5-methyl-hexanoate with purity ~80% by GC and chiral GC purity data (%): S:R 50.74:49.26.

Example 4.10: Preparation of methyl-3-cyano-5-methyl-hexanoate from R Enriched (IX)

Assembled a 1 lit three neck RBF, equipped with magnetic needle, thermometer pocket and reflux condenser over an oil bath. R-Enriched 3-cyano-5-methyl-hexanoic acid (100.0 g; 1.0 eqv.) was dissolved in EtOH (500 ml) and NaHCO$_3$ (54.12 g) and NaOEt (32.85 g; 0.75 eqv) was added at 25° C. The reaction mass was refluxed for 4.5 h at 78° C. The majority of ethanol was distilled. The reaction mixture was cooled to 25° C. and water (200 ml) was added and distilled out EtOH and water (100 ml). It was acidified with 1N HCl solution till pH 1-2 and extracted by MTBE (150 ml×3). The combined MTBE layer was dried over anhydrous sodium sulphate. It was concentrated under reduced pressure at 40° C. to give 100 g racemic 3-cyano-5-methyl-hexanoic acid. To the residue MeOH (500 ml) was added followed by H$_2$SO$_4$ (8 g) at 25° C. The reaction mixture was refluxed for 1 h. The reaction mass was concentrated under vacuum ~45° C. (<500 torr; 70% MeOH was recovered) and added water (200 ml). The oily layer was extracted using toluene (150 ml×2). Combined organic layer was washed with saturated sodium bicarbonate solution (pH 7-8). The organic layer was under reduced pressure (~500 torr) at 40° C. to give 88.96% yield (over two steps) of crude methyl-3-cyano-5-methyl-hexanoate with purity ~86.37% by GC. The crude material was further purified by distillation under vacuum to get pure product in 68% with purity >96% by GC.

Example 4.11: Preparation of methyl-3-cyano-5-methyl-hexanoate from R Enriched (IX)

Assembled a 5 lit three neck RBF, equipped with mechanical stirrer, thermometer pocket and reflux condenser over an oil bath. R-Enriched 3-cyano-5-methyl-hexanoic acid (500.0 g; 1.0 eqv.) was dissolved in EtOH (3000 ml) and NaHCO$_3$ (270.62 g) and NaOEt (164.42 g; 0.75 eqv) was added at 25° C. The reaction mass was refluxed for 4.0 h at 78° C. The majority of ethanol was distilled. The reaction mixture was cooled to 25° C. and water (1000 ml) was added and distilled out EtOH and water (500 ml). It was acidified with 1N HCl solution till pH 1-2 and extracted by MTBE (500 ml×2). The combined MTBE layer was optionally dried over anhydrous sodium sulphate. It was concentrated under reduced pressure at 40° C. to give 100 g racemic 3-cyano-5-methyl-hexanoic acid. To the residue MeOH (2500 ml) was added followed by H$_2$SO$_4$ (40 g) at 25° C. The reaction mixture was refluxed for 1 h. The reaction mass was concentrated under vacuum ~45° C. (<500 torr) and added water (800 ml). The oily layer was extracted using toluene (750 ml×2). Combined organic layer was washed with saturated sodium bicarbonate solution (pH 7-8). The organic layer was under reduced pressure (~500 torr) at 40° C. to give 445 g (81.62% yields over two steps) of crude methyl-3-cyano-5-methyl-hexanoate with purity ~81.02% by GC, The crude material was further purified by distillation under vacuum to get 342 g (62.73%) pure product with purity >97.8% by GC.

TABLE 2

Screening of enzymes for synthesis of compound VIII

| Batch size (g) | Type of enzyme | Crude yield (g)/%; GC purity (%, comp, Rt)/chiral purity |
|---|---|---|
| 0.1 | *Candida Antarctica* B1 | 0.0085/8.5; R-ester: 0.42/S-ester: 99.58 |
| 0.1 | *Candida Antarctica* BY2 | 0.01/10; R-ester: 2.77/S-ester: 97.23 |
| 0.0 | lipase 3.111[#] | Low conversion |
| 0.05 | lipase 3.113[#] | Low conversion |
| 0.05 | lipase 3.104[#] | Low conversion |
| 0.05 | lipase 3.106[#] | Low conversion |
| 0.05 | lipase 3.108[#] | Low conversion |
| 0.05 | lipase 3.110[#] | Low conversion |
| 0.05 | lipase 3.101[#] | Low conversion |
| 0.05 | lipase 3.102[#] | Low conversion |

[#]Enzymes from Evocatal

Enzyme catalyzed hydrolysis was explored with 100 mg of compound V with 20% loading of 28 different enzymes at pH 7 phosphate buffer (1 ml, 10 V) from Among these different enzymes investigated CAL B1, CAL BY2 furnished good results. However chiral purity with CAL BY2 was found to be low as compared to CAL B1.Hence only CAL B1 was considered for further investigations.

Enzymes obtained from chiralvision *candida antarctica* A, *rhizomucor miehei*, *thermomyces Lanhginosa*, *pseudomonas cepacia*, resinase HT, lipex 100L, novozymes, *bacillus subtillis* enzymes from Evocatal lipase 3.1i1, lipase 3.105, lipase 3.107, lipase 3.109 and enzymes from Amano amano lipase PS, amano lipase AK, amano lipase AH, amano lipase AYS did not respond to this substrate under the chosen condition Enzyme catalyzed hydrolysis was also explored with 100 mg of compound V with 20% loading of different enzymes at pH 8 phosphate buffer (1 ml, 10 V) and acid formation was observed only with *Candida antarctica*,B1 in both buffer solution viz. pH 7 and 8 on GC. Among the reactions investigated at pH 7 and 8, rate of reaction (enzyme activity w.r.t reaction rate) was found to be higher at pH 7 rather than at pH 8. No other enzymes responded in pH 8 with other conditions remaining the same

TABLE 3

Enzymatic hydrolysis in different solvent:

Conditions

| Lipase (g) | Phosphate buffer (pH 7.0) ml (V) | Solvents ml (V) | Temp (° C.) | Time h | Remark/GC Purity [%] |
|---|---|---|---|---|---|
| 0.020 *Candida antarctica*, B1 | 0.75 (7.5) | 0.25 (2.5) Acetone | 25 | 24 | 86.64 IV (08.00) |
| 0.020 *Candida antarctica*, B1 | 0.75 (7.5) | 0.25 (2.5) THF | 25 | 24 | 86.07 IV (08.00) |
| 0.020 *Candida antarctica*, B1 | 0.75 (7.5) | 0.25 (2.5) DMSO | 25 | 24 | 11.08 ester (08.00) 47.57 acid (08.76) |
| 0.020 *Candida antarctica*, B1 | 0.75 (7.5) | 0.25 (2.5) 1,4-dioxane | 25 | 24 | 53.33 ester (08.00) 33.47 acid (08.70) |

Lipase catalyzed hydrolysis was explored with CAL B1 in combination (75:25) of buffer and different solvents on 0.1 g scale.
Only DMSO provided ~47% conversion and other impurity formed with 20% enzyme loading.
In 1,4-dioxane considerable conversion with less % of impurity formation was observed hence selected for further investigation.

TABLE 4

Enzymatic hydrolysis using 20% *Candida antarctica* in presence of reaction media of 3:1 1.75% aq. NaHCO$_3$ at (pH adjusted to 7.0 at the beginning of reaction and no control afterwards): 1,4-dioxane in different volumes:

| Comp. VII amount | Lipase (g) | NaHCO$_3$ pH = 7 ml/v | 1,4-dioxane ml/v | Time/ temp | Yield (g/%) GC purity [%, comp. (Rt)] Ester (S); (chiral GC purity) |
|---|---|---|---|---|---|
| 40.0 (1.0) | *Candida antarctica*, B1 (8.0) | 60.0/7.5 | 20.0/2.5 | 25/24 | 16.5/41.25 93.51 VII (10.32) R-ester: 1.68; S-ester: 98.32 |
| 2 (1.0) | *Candida antarctica*, B1 (0.4) | 22.5/7.5 | 7.5/2.5 | 25/5 | 97.61 (10.18) R-ester: 1.83; S-ester: 98.17 |
| 2 (1.0) | *Candida antarctica*, B1 (0.4) | 37.5/7.5 | 12.5/2.5 | 25/5 | 0.862/43.1 96.83 ester (10.18) R-ester: 0.67; S-ester: 99.33 |
| 0.1/(1.0) | Novozyme 435 (0.020 g) | 1.875/(7.5) | 0.625/2.5 | 25/24 | 0.049/49.0 60.20 ester (10.16) R-ester: 12.34; S-ester: 87.66 |

Lipase catalyzed hydrolysis was explored in different solvent volumes, among these only 25 V reaction provided good chiral purity 99.33% (ee 98.66%) with 20% enzyme loading in 5 h. Novozyme 435 also furnished good conversion and chiral purity in its first experiment.

TABLE 5

Enzymatic hydrolysis using different loading of *Candida antarctica* in presence of reaction media of 3:1 1.9% aq. NaHCO$_3$ at (pH adjusted to 7.0 at the beginning of reaction and no control afterwards): 1,4-dioxane in different volumes:

| Batch Size | Conditions Lipase g (%) | NaHCO$_3$ (pH 7.0) mL/(V) | 1,4-dioxane mL/(V) | Temp./ Time (° C./h) | Yield (g/%) Chiral GC Purity |
|---|---|---|---|---|---|
| 10.0 | 0.5 g (5%) *Candida antarctica*, B1 | 187.5/(7.5) | 62.5/(2.5) | 25/96 | 3.8/38.0 90.24 ester (10.19) R-ester: 1.01; S-ester: 98.99 |
| 1.0 | 0.4 ml (2%) Novocor ADL | 18.75/(7.5) | 6.25/(2.5) (25 V) | 25/96 | 0.44/44.0 95.63 ester (10.15) R-ester: 14.33; S-ester: 85.67 |
| 0.2 | 0.4 ml (10%) Novocor ADL | 3.75/(7.5) | 1.25/(2.5) (25 V) | 25/96 | 0.060/30.0 95.79 ester (10.15) R-ester: 12.02; S-ester: 87.98 |
| 0.2 | 0.4 ml (10%) Novocor ADL | 3.75/(7.5) | 1.25/(2.5) (25 V) | 40/96 | 0.062/31.0 97.71 ester (10.14) R-ester: 12.26; S-ester: 87.74 |
| 0.5 | 5.0 ml (50%) Novocor ADL | 9.375/(7.5) | 3.125/(2.5) (25 V) | 25/96 | 0.14/28.0 71.16 ester (10.14) Rester: 5.23; S-ester: 94.77 |
| 1.0 | 0.05 g (5%) Novozyme 435 | 7.5/(7.5) (10 V) | 2.5/(2.5) | 25/48 | 0.44/44.0 84.08 ester (10.14) R-ester: 6.53; S-ester: 93.47 |
| 1.0 | 0.05 g (5%) Novozyme 435 | 15.0/(15) (20 V) | 5.0/(5) | 25/24 | 0.38/38.0 86.89 ester (10.15) R-ester: 1.41; S-ester: 98.59 |
| 1.0 | 0.05 g (5%) Novozyme 435 | 22.5/(22.5) (30 V) | 7.5/(7.5) | 25/48 | 0.38/38.0 80.57 ester (10.12) R-ester: 1.80; S-ester: 98.20 |
| 1.0 | 0.075 g (7.5%) Novozyme 435 | 7.5/(7.5) (10 V) | 2.5/(2.5) | 25/24 | 0.41/41.0 83.57 ester (10.15) R-ester: 6.45; S-ester: 93.55 |
| 1.0 | 0.075 g (7.5%) Novozyme 435 | 15.0/(15) (20 V) | 5.0/(5) | 25/24 | 0.388/38.8 83.69 ester (10.16) R-ester: 2.08; S-ester: 97.92 |
| 1.0 | 0.075 g (7.5%) Novozyme 435 | 22.5/(22.5) (30 V) | 7.5/(7.5) | 25/50 | 0.45/45.0 62.38 ester (10.11) R-ester: 9.76; S-ester: 90.24 |
| 1.0 | 0.02 g (2%) Novozyme 435 | 3.75/(3.75) (5 V) | 125/(1.25) | 25/69 | 0.25/25.0 83.30 ester (10.14) R-ester: 11.56; S-ester: 88.44 |
| 1.0 | 0.02 g (2%) Novozyme 435 | 7.5/(7.5) (10 V) | 2.5/(2.5) | 25/24 | 65.66 ester (10.12) 16.83 acid (11.43) Low conversion |

TABLE 5-continued

Enzymatic hydrolysis using different loading of *Candida antarctica* in presence of reaction media of 3:1 1.9% aq. NaHCO$_3$ at (pH adjusted to 7.0 at the beginning of reaction and no control afterwards): 1,4-dioxane in different volumes:

| Batch Size | Conditions | | | Temp./ Time (° C./h) | Yield (g/%) Chiral GC Purity |
|---|---|---|---|---|---|
| | Lipase g (%) | NaHCO$_3$ (pH 7.0) mL/(V) | 1,4-dioxane mL/(V) | | |
| 1.0 | 0.02 g (2%) Novozyme 435 | 15.0/(15) (20 V) | 5.0/(5) | 25/96 | 60.60 7 (10.11) 16.24 6 (11.45) Low conversion |
| 10.0 | 0.2 g (2%) Novozyme 435 | 187.5/(18.75) (25 V) | 62.5/(6.25) | 25/96 | 3.75/37.5 91.86 ester (10.19) R-ester: 1.53 S-ester: 98.47 |

5% loading of *Candida antarctica* B1, provided 38% yield of S-ester (ee 97.98%) with longer reaction time i.e. 96 h. Due to no recyclability the cost of Novocor ADL was found to be very high as compared to Novozyme 435. Hence only Novozyme 435 was considered for further investigations The enzymatic hydrolysis of compound V was studied with 2, 5 and 7.5% enzyme loading (Novozyme 435) in aq. NaHCO$_3$ buffer (pH 7.0) and 1,4-dioxane (3:1) in 10, 20, 30 V respectively, it was observed that the chiral GC purity of comp. X increased from ~93 to ~98%.

TABLE 6

Enzymatic hydrolysis (parameter studies using *Candida antarctica*: in presence of 1.75% aq. NaHCO$_3$ (pH adjusted to 7.1 ± 0.1 at the beginning of reaction and no control afterwards) with respect to enzyme and time):

| Batch size | Lipase g/ml | NaHCO$_3$ pH 7.0 mL/(V) | Temp./time (° C./h) | Yield (g/%) GC Purity [%, comp. (Rt)] Chiral GC purity |
|---|---|---|---|---|
| 1.0 | 0.05 g (5%) Novozyme 435 | 20.0/(20) | 25/7 | 0.34/34.0 87.96 ester (10.14) R-ester: 2.82; S-ester: 97.18 |
| 1.0 | 0.05 g (5%) Novozyme 435 | 20.0/(20) | 25/41 | 0.25/25.0 70.68 ester(10.11) R-ester: 8.80; S-ester: 91.20 |
| 1.0 | 0.05 g (5%) Novozyme 435 | 20.0/(20) | 25/2 | 0.4/40.0 90.90 ester (10.13) R-ester: 1.01; S-ester: 98.91 |
| 1.0 | 0.05 g (5%) Novozyme 435 | 20.0/(20) | 25/4 | 0.38/38.0 88.59 ester (10.13) R-ester: 1.96; S-ester: 98.04 |
| 1.0 | 0.05 g (5%) Novozyme 435 | 20.0/(20) | 25/6 | 0.34/34.0 86.87 ester (10.14) R-ester: 2.90 S-ester: 97.10 |
| 1.0 | 0.04 g (4%) Novozyme 435 | 20.0/(20) | 25/2 | 0.50/50.0 93.03 ester (10.16) R-ester: 12.50; S-ester: 87.50 |
| 1.0 | 0.03 g (3%) Novozyme 435 | 20.0/(20) | 25/2 | 0.50/50.0 90.88 ester (10.17) R-ester: 8.90; S-ester: 91.10 |
| 1.0 | 0.03 g (3%) Novozyme 435 | 20.0/(20) | 25/6 | 0.33/33.0 92.51 ester (10.13) R-ester: 0.71; S-ester: 99.29 |
| 1.0 | 0.02 g (2%) Novozyme 435 | 20.0/(20) | 25/2 | 0.50/50.0 93.01 ester (10.18) R-ester: 28.68; S-ester: 71.32 |
| 1.0) | 0.02 g (2%) Novozyme 435 | 20.0/(20) | 25/6 | 0.36/36.0 92.48 ester (10.14) R-ester: 0.58; S-ester: 99.42 |
| 1.0 | 0.01 g (1%) Novozyme 435 | 20.0/(20) | 25/4 | 0.50/50.0 94.22 ester (10.13) R-ester: 21.72; S-ester: 78.28 |
| 1.0 | 0.01 g (1%) Novozyme 435 | 20.0/(20) | 25/6 | 0.50/50.0 93.98 ester (10.15) R-ester: 18.14; S-ester: 81.59 |
| 1.0 | 0.01 g (1%) Novozyme 435 | 20.0/(20) | 25/18 | 0.42/42.0 94.08 ester (10.14) R-ester: 3.13; S-ester: 96.87 |
| 1.0 | 0.01 g (1%) Novozyme 435 | 20.0/(20) | 25/24 | 0.40/40.0 93.35 ester (10.15) 1.18 ? (10.57) R-ester: 2.49; S-ester: 97.51 |

TABLE 6-continued

Enzymatic hydrolysis (parameter studies using *Candida antarctica*: in presence of 1.75% aq. NaHCO$_3$ (pH adjusted to 7.1 ± 0.1 at the beginning of reaction and no control afterwards) with respect to enzyme and time):

| Batch size | Lipase g/ml | NaHCO$_3$ pH 7.0 mL/(V) | Temp./time (° C./h) | Yield (g/%) GC Purity [%, comp. (Rt)] Chiral GC purity |
|---|---|---|---|---|
| 1.0 | 0.005 g (0.5%) Novozyme 435 | 20/(20) | 25/42 | 0.32/32.0 91.65 ester (10.14) R-ester: 1.50; S-ester: 98.50 |
| 1.0/ | 0.01 g (1%) Novozyme 435 | 10/(10) | 25/24 | 0.37/37.0 87.10 ester (10.14) R-ester: 16.92; S-ester: 83.08 |

Parameter studies using *candida antarctica*: in presence of various strength of aq. NaHCO$_3$ (pH adjusted to 7.1 ± 0.1 at the beginning of reaction and no control afterwards) with respect to enzyme loading and time Sodium bicarbonate (conc. 1.89%) with 1% and 2% loading in 20

| 25.0 | 0.25 g (1%) Novozyme 435 | 500/(20) | 25/19 | 9.57/38.2 94.69 ester (10.15) R-ester: 0.82; S-ester: 99.18 |
| 25.0 | 0.5 g (2%) Novozyme 435 | 500/(20) | 25/10 | 9.7/38.8 94.08 ester (10.15) R-ester: 1.37; S-ester: 98.63 |

Sodium bicarbonate (conc. 3.75%) with 1% and 2% enzyme loading in 20 V.

| 50.0 | 0.5 g (1%) Novozyme 435 | 1000/(20) | 25/6.5 | 20.0/40.0 88.76 ester (10.13) R-ester: 0.15; S-ester: 99.85 |
| 50.0 | 1.0 g (1%) Novoyme 435 | 1000/(20) | 25/5 | 19.1/38.2 88.70 ester (10.15) R-ester: 0.23; S-ester: 99.77 |

Sodium bicarbonate (7% conc.) aq. NaHCO$_3$ buffer (pH 7.1 ± 0.1 at the beginning of reaction and no control afterwards) with 1% enzyme (Novozyme 435) loading in 5, 7.5, 10 and 15 V.

| 3.0 | 0.03 g (1%) Novozyme 435 | 15.0/(5) | 25/25 | R-ester: 5.74; S-ester: 94.26 Note 1 |
| 3.0 | 0.03 g (1%) Novozyme 435 | 22.5/(7.5) | 25/13.5 | R-ester: 0.49; S-ester: 99.51 Note 1 |
| 3.0 | 0.03 g (1%) Novozyme 435 | 30.0/(10) | 25/10 | R-ester: 0.46; S-ester: 99.54 Note 1 |
| 3.0 | 0.03 g (1%) Novozyme 435 | 45.0/(15) | 25/10 | R-ester: 0.77; S-ester: 99.23 Note 3 |

TABLE 7

To check the activity and enantioselectivity of enzyme Novozyme 435 (2% loading) for hydrolysis of compound 7 in presence of aq. NaHCO$_3$ (conc. 7%) at pH of 7.0, 7.5 and 8.0

| Batch size | Lipase g/ml | NaHCO$_3$ pH mL/(V) | Temp./ time (° C./h) | Yield (g/%) GC Purity [%, comp. (Rt)] Chiral GC purity |
|---|---|---|---|---|
| 5.0 | 0.1 Novozyme 435 | 75/(15) 7.0* | RT/12 | 1.95/39.0 91.05 ester (10.12) R-ester: 0.11; S-ester: 99.89 |
| 5.0 | 0.1 g Novozyme 435 | 75/(15) 8.0# | RT/12 | 1.91/38.2 91.51 ester (10.10) R-ester: 0.27; S-ester: 99.73 |
| 5.0 | 0.1 g Novozyme 435 | 75/(15) 7.5$ | RT/5 | 1.6/32.0 87.30 7 (10.12) R-ester: 0.09; S-ester: 99.91 |

*Maintained the pH at 7.0 throughout;
The initial pH of 8.5 was not maintained further during the reaction;
$Maintained the pH at 7.5 throughout

Example 5.1: Preparation of (S)-methyl 3-cyano-5-methyl-hexanoate and (R)-3-cyano-5-methyl-hexanoic acid Arranged a 25 ml single neck RBF, equip with magnetic needle on magnetic stirrer. Racemic methyl 3-cyano-5-methyl-hexanoate (0.5 g; 1.0 eq) was dispersed in phosphate buffer (3.75 ml; pH=7.0) and 1,4-dioxane (0.125 ml) followed by *Candida antarctica* B1 (0.1 g). The reaction mass was stirred for 5 h. The reaction mass was diluted with ethyl acetate and filtered under suction. The layers were separated. The organic layer was washed with saturated sodium bicarbonate solution 15 ml (5 ml×3). The organic layer was optionally dried over anhydrous sodium sulphate and concentrated. The isolated yield is 0.17 g (43% S-ester; chemical purity 96.83% with >98.6% ee) of compound VIII (R$_3$=methyl).

Example 5.2: Preparation of (S)-methyl 3-cyano-5-methyl-hexanoate and (R)-3-cyano-5-methyl-hexanoic acid Arranged a 25 ml single neck RBF, equip with magnetic needle on magnetic stirrer. Racemic methyl 3-cyano-5-methyl-hexanoate (0.5 g; 1.0 eqv.) was dispersed in aqueous 1.9% NaHCO$_3$ (9.4 ml; pH=7.0) and 1,4-dioxane (3.13 ml) followed by Novozyme 435 (0.01 g). The reaction mass was stirred for 24 h. At the end of the reaction pH of the reaction was observed to be ~8.3. The reaction mass was diluted with ethyl acetate and filtered under suction. The layers were separated. The organic layer was washed with saturated sodium bicarbonate solution 15 ml (5 ml×3). The organic layer was optionally dried over anhydrous sodium sulphate and concentrated. The isolated yield is 37.5% S-ester; chemical purity 91.86% with >98.14% ee) of compound VIII ($R_3$=methyl). From aqueous layer enriched R acid was isolated in 56.7% with purity 78% by GC.

Example 5.3: Preparation of (S)-methyl 3-cyano-5-methyl-hexanoate and (R)-3-cyano-5-methyl-hexanoic acid Arranged a 25 ml single neck RBF, equip with magnetic needle on magnetic stirrer. Racemic methyl 3-cyano-5-methyl-hexanoate (5 g; 1.0 eqv.) was dispersed in aqueous 7% $NaHCO_3$ (75 ml; pH=7.5) followed by Novozyme 435 (0.1 g). The reaction mass was stirred for 12 h. During the reaction the pH was maintained at 7.5 The reaction mass was diluted with ethyl acetate and filtered under suction. The layers were separated. The organic layer was washed with saturated sodium bicarbonate solution 15 ml (5 ml×3). The organic layer was optionally dried over anhydrous sodium sulphate and concentrated. The isolated yield is 32.0% S-ester; chemical purity 87.30% with chiral purity 99.91%) of compound VIII ($R_3$=methyl). From aqueous layer enriched R acid was isolated in 62.57% with purity 78%.

Example 5.4: Preparation of (S)-methyl 3-cyano-5-methyl-hexanoate and (R)-3-cyano-5-methyl-hexanoic acid Arranged a 25 ml single neck RBF, equip with magnetic needle on magnetic stirrer. Racemic methyl 3-cyano-5-methyl-hexanoate (5 g; 1.0 eqv.) was dispersed in aqueous 7% $NaHCO_3$ (75 ml; pH=7.0) followed by Novozyme 435 (0.01 g). The reaction mass was stirred for 12 h. During the reaction the pH was maintained at 7.0. The reaction mass was diluted with ethyl acetate and filtered under suction. The layers were separated. The organic layer was washed with saturated sodium bicarbonate solution 15 ml (5 ml×3). The organic layer was optionally dried over anhydrous sodium sulphate and concentrated. The isolated yield is 39.0% S-ester; chemical purity 91.05% with chiral purity 99.94%) of compound VIII ($R_3$=methyl). From aqueous layer enriched R acid was isolated in 58.7% with purity 78% by GC and chiral purity 80.86% ee.

Example 5.5: Preparation of (S)-methyl 3-cyano-5-methyl-hexanoate

Arranged a 25 ml single neck RBF, equip with magnetic needle on magnetic stirrer. Racemic methyl 3-cyano-5-methyl-hexanoate (5 g; 1.0 eqv.) was dispersed in aqueous 7% $NaHCO_3$ (75 ml; pH=8.0) followed by Novozyme 435 (0.01 g). The reaction mass was stirred for 12 h. During the reaction the pH was maintained at 8.0. The reaction mass was diluted with ethyl acetate and filtered under suction. The layers were separated. The organic layer was washed with saturated sodium bicarbonate solution 15 ml (5 ml×3). The organic layer was optionally dried over anhydrous sodium sulphate and concentrated. The isolated yield is 38.2% S-ester; chemical purity 91.51% with chiral purity 99.73%) of compound VIII ($R_3$=methyl). From aqueous layer enriched R acid was isolated in 57.8% with purity 78% by GC and chiral purity 80.86% ee.

Example 5.6

In a 250 ml single neck RBF, equipped with magnetic needle over a magnetic stirrer, methyl 3-cyano-5-methyl-hexanoate (10 g; 1.0 eqv) was dispersed in 150 ml aqueous 7% $NaHCO_3$ solution (pH 7.0) containing 10.5 g $NaHCO_3$ and 0.2 g of Novozyme 435 was added at 25° C. The reaction mass was stirred for 7 h at 26±2° C. till hydrolysis was >50% monitored through chiral GC analysis. At the end of the reaction pH of the reaction was observed to be ~8.0. The reaction mass was filtered through Buchner funnel using vacuum and the residual enzyme was washed with ethyl acetate (50 ml). The two layers were separated. The aqueous layer was extracted with ethyl acetate (3×20 ml). The combined organic layer was washed with saturated bicarbonate solution 60 ml and optionally dried over anhydrous sodium sulphate and concentrated under reduced pressure to give 20 g (40.1%) of compound VIII with purity of 91.73% by GC; and chiral purity of 99.91% (99.82% ee). The aqueous layer was acidified by 1N HCl solution till pH 1-2 and extracted with ethyl acetate (60 ml) and dried over anhydrous sodium sulphate. Distillation of EtOAc under reduced pressure gave 5.4 g of R-enriched X ($R_2$=H).

Example 5.7

In a 10 lit RBF, equipped with mechanical stirrer, methyl 3-cyano-5-methyl-hexanoate (450 g; 1.0 eqv) was dispersed in 6750 ml aqueous 7% $NaHCO_3$ solution (pH 7.0) and 9.0 g of Novozyme 435 was added at 25° C. The reaction mass was stirred for 6 h at 26±2° C. till hydrolysis was >50% monitored through chiral GC analysis. During the maintenance no pH adjustment was done. The reaction mass was filtered through Buchner funnel using vacuum and the residual enzyme was washed with ethyl acetate (800 ml). The two layers were separated. The aqueous layer was extracted with ethyl acetate (2×100 ml). The combined organic layer was washed with saturated bicarbonate solution optionally dried over anhydrous sodium sulphate and concentrated under reduced pressure to give 180 g (41.0%) of compound VIII with purity of 98.74% by GC; and chiral purity of 99.95%. The aqueous layer was acidified by 1N HCl solution till pH 1-2 and extracted with ethyl acetate (2×300 ml) and dried over anhydrous sodium sulphate. Distillation of EtOAc under reduced pressure gave 234 g of R-enriched X ($R_2$=14).

Example 5.9

Arranged a 25 ml single neck RBF, equip with magnetic needle on magnetic stirrer. Racemic methyl 3-cyano-5-methyl-hexanoate (10 g; 1.0 eqv.) was dispersed in aqueous 7% $NaHCO_3$ (150 ml; pH=7.0) followed by Novozyme 435 (0.2 g). The reaction mass was stirred for 12 h. During the reaction the pH was not maintained. The reaction mass was diluted with ethyl acetate and filtered under suction. The layers were separated. The organic layer was washed with saturated sodium bicarbonate solution 50 ml (25 ml×2). The organic layer was optionally dried over anhydrous sodium sulphate and concentrated. The isolated yield is 2.3 g (23%) % S-ester; chemical purity 96.94% with chiral purity 100%) of compound VIII ($R_3$=methyl). From aqueous layer enriched R acid was isolated in 72.8%

Example 5.10

Arranged a 25 ml SS vessel, equip with mechanical stirrer. Racemic methyl 3-cyano-5-methyl-hexanoate (5 g; 1.0 eqv.) was dispersed in aqueous 7% $NaHCO_3$ (75 ml; pH=7.0) followed by Novozyme 435 (0.1 g). The reaction mass was stirred for 6 h at 25° C. During the reaction the pH was not maintained. The reaction mass was diluted with ethyl acetate and filtered under suction. The layers were separated. The organic layer was washed with saturated sodium bicarbonate solution 30 ml (15 ml×2). The organic layer was optionally dried over anhydrous sodium sulphate and concentrated. The isolated yield is 1.99 g (39.8%) of S-ester; chemical purity 98.21% with chiral purity 99.8%) of compound VIII ($R_3$=methyl). From aqueous layer enriched R acid was isolated in 57.2%.

TABLE 7

To check the activity and enantioselectivity of enzyme (Novozyme 435 2%) for hydrolysis of compound V in presence of aq. $NaHCO_3$ (conc. 7%) (initially adjusted pH = 7.2 ± 0.2) 15 V at 350 RPM

| Run | Time (h) | Yield of S-Ester (%) | GC Purity of S-Ester (%) | Chiral GC Purity of S-Ester (%) |
|---|---|---|---|---|
| 1 | 7 | 40.6 | 90.38 VII (10.13) | R-ester: 0.22; S-ester: 99.78 |
| 2 | 7 | 40.5 | 90.44 VII (10.11) | R-ester: 0.17; S-ester: 99.83 |
| 3 | 7 | 40.6 | 88.93 VII (10.13) | R-ester: 0.14; S-ester: 99.86 |
| 4 | 7 | 40.4 | 90.30 VII (10.13) | R-ester: 0.18; S-ester: 99.82 |
| 5 | 7 | 40.4 | 85.17 VII (10.12) | R-ester: 0.11; S-ester: 99.89 |
| 6 | 7 | 40.5 | 89.15 VII (10.16) | R-ester: 0.12; S-ester: 99.88 |
| 7 | 7 | 40.6 | 85.14 VII (10.12) | R-ester: 0.28; S-ester: 99.72 |
| 8 | 7 | 40.6 | 90.99 VII (10.11) | R-ester: 0.04; S-ester: 99.96 |
| 9 | 7 | 40.5 | 90.66 VII (10.13) | R-ester: 0.26; S-ester: 99.74 |
| 10 | 7 | 40.4 | 94.68 VII (10.12) | R-ester: 0.20; S-ester: 99.80 |
| 11 | 7 | 40.4 | 94.46 VII (10.11) | R-ester: 0.09; S-ester: 99.91 |
| 12 | 7 | 40.5 | 94.68 VII (10.12) | R-ester: 0.07; S-ester: 99.93 |
| 13 | 7 | 42.1 | 96.24 VII (10.12) | R-ester: 2.45; S-ester: 97.55 |
| 14 | 7 | 40.4 | 93.79 VII (10.11) | R-ester: 0.15; S-ester: 99.85 |
| 15 | 7 | 40.3 | 91.06 VII (10.12) | R-ester: 0.23; S-ester: 99.77 |
| 16 | 7 | 40.4 | 85.07 VII (10.16) | R-ester: 0.25; S-ester: 99.75 |
| 17 | 7 | 40.5 | 88.67 VII (10.12) | R-ester: 0.16; S-ester: 99.84 |
| 18 | 7 | 40.3 | 88.68 VII (10.12) | R-ester: 0.35; S-ester: 99.65 |
| 19 | 5.5 | 40.7 | 88.59 VII (10.12) | R-ester: 0.26; S-ester: 99.74 |
| 20 | 5.5 | 40.8 | 89.65 VII (10.11) | R-ester: 0.23; S-ester: 99.77 |
| 21 | 5.5 | 40.7 | 89.45 VII (10.11) | R-ester: 0.33; S-ester: 99.67 |
| 22 | 5.5 | 40.3 | 79.94 VII (10.12) | R-ester: 0.31; S-ester: 99.69 |
| 23 | 5.5 | 40.3 | 95.99 VII (10.16) | R-ester: 0.06; S-ester: 99.94 |
| 24 | 5.5 | 40.4 | 94.13 VII (10.10) | R-ester: 0.15; S-ester: 99.85 |
| 25 | 5.5 | 35.5 | 85.40 VII (10.10) | R-ester: 0.04; S-ester: 99.96 |
| 26 | 5.5 | 36.0 | 94.93 VII (10.09) | R-ester: 0.12; S-ester: 99.88 |

Example 6.1: Preparation of Racemic Pregabalin

To a clean 1 lit autoclave placed caustic solution prepared by dissolving 14.18 g of sodium hydroxide in 350 ml of water. The solution was cooled to 20-25° C. and racemic 3-cyano-5-methyl-hexanoic acid (50 g) was added into the autoclave. Raney Ni (15.0 g; 30% w/w) was added. The autoclave was closed properly and started stirring. The air inside the autoclave was replaced by purging nitrogen gas twice. It was pressurized 5 kg/cm² of hydrogen gas and release to atmosphere twice to remove nitrogen gas. The stirring was initiated with 700 RPM at 30° C. and hydrogen gas pressure of 10 kg/cm². The hydrogenation was continued till completion of reaction checked by HPLC. The catalyst was filtered through celite or any other suitable bed and washed with water (50 ml). The catalyst was recovered for reuse. The reaction mass was extracted with MTBE (150 ml). The aqueous layer was acidified to pH 1.0 with 60-65 ml conc. HCl. Cool the reaction mass to 0° C. and adjust the pH at 7.4 by adding 10% NaOH solution (~25 ml). Racemic Pregabalin) started separating as white crystals. The reaction mass was maintained at 0° C. for 2-3 hr. The solid was filtered through a Buchner funnel under vacuum. The wet cake was washed with 50 ml of water and suck dried for 30 min to get 55.0 g of wet cake. The wet cake of racemic pregabalin was dried at 45° C. under vacuum for 3-5 hrs to get 35.5 g (71.1% yield; purity 98.09% by HPLC). ¹H-NMR (D₂O, 400 MHz): 2.945 (2H, d), 2.378 (2H, m), 2.078 (1H, m), 1.566 (1H, m), 1.170 (2H, dd), 0.809 (6H, dd).

Example 6.2: Preparation of Racemic Prgabalin

To a clean 400 ml autoclave, 3-cyano-5-methyl hexanoic acid methyl ester 10.0 g (1 eq.) was dissolved in methanol (100 ml) at 25° C. A solution of potassium hydroxide (2.85 g in 4.75 ml water; ~60%) was added by controlling the addition rate to maintain the reaction mass temperature below 25° C. It was stirred at 20-25° C. for about 1.5 h. Raney Ni (3.0 g; 30% w/w) was added. The autoclave was closed properly and started stirring. The air inside the autoclave was replaced by purging nitrogen gas twice. It was pressurized 10 kg/cm² of hydrogen gas and release to atmosphere twice to remove nitrogen gas. The stirring was initiated with 500 RPM at 30° C. and hydrogen gas pressure of 10 kg/cm². The hydrogenation was continued till almost full conversion (checked by HPLC). The catalyst was filtered through celite or any other suitable bed and washed with MeOH water (25 ml). The catalyst was recovered for reuse. The filtrate was adjusted to pH 7-7.4 by using glacial acetic acid (~5 ml). The methanol was recovered under reduced pressure at 40° C. The reaction mass was cooled to 0 to 5° C. for 1 h. The solid was filtered on a Buchner funnel using vacuum. The wet cake washed with 15-20 ml of chilled isopropyl alcohol and suck dried for 30 min. Dry weight of racemic Pregabalin thus obtained was 5.17 g (55% yield; chemical purity 99.26% by HPLC Example 6.3: Preparation of S-pregabalin To a clean 1 lit autoclave, (S)-3-cyano-5-methyl hexanoic acid methyl ester 60.0 g (1 eq.) was dissolved in methanol (600 ml) at 25° C. A solution of potassium hydroxide (27.14 g in 85 ml water; ~32%) was added by controlling the addition rate to maintain the reaction mass temperature below 25° C. It was stirred at 20-25° C. for about 1.5 h. Raney Ni (18.0 g; 30%; w/w with respect to substrate) was added. The autoclave was closed properly and started stirring. The air inside the autoclave was replaced by purging nitrogen gas twice. It was pressurized 10 kg/cm² of hydrogen gas and release to atmosphere twice to remove nitrogen gas. The stirring was initiated with 500 RPM at 30° C. and hydrogen gas pressure of 10 kg/cm². The hydrogenation was continued till almost full conversion (checked by HPLC). The catalyst was filtered through celite or any other suitable bed and washed with MeOH water (80 ml). The catalyst was recovered for reuse. The filtrate was adjusted to pH 7-7.4 by using glacial acetic acid (~30 ml). The methanol was recovered under reduced pressure at 40° C. The reaction mass was cooled to 0 to 5° C. for 1 h. The solid was filtered on a Buchner funnel using vacuum. The wet cake washed with 60 ml of chilled isopropyl alcohol and suck dried for 30 min. Dry weight of (S)-Pregabalin thus obtained was 45.16 g (80.0% yield; chemical purity 99.27% by HPLC; chiral purity 99.81% by HPLC).

Example 6.4: Preparation of S-pregabalin

To a clean 1 lit autoclave, (S)-3-cyano-5-methyl hexanoic acid methyl ester 20.0 g (1 eq.) was dissolved in methanol (200 ml; 10 V) at 25° C. A solution of potassium hydroxide (9.05 g in 28.28 ml water; ~32%) was added by controlling the addition rate to maintain the reaction mass temperature below 25° C. It was stirred at 20-25° C. for about 1.5 h. Raney Ni (6.0 g; 30%; w/w with respect to substrate) was added. The autoclave was closed properly and started stirring. The air inside the autoclave was replaced by purging nitrogen gas twice. It was pressurized 10 kg/cm² of hydrogen gas and release to atmosphere twice to remove nitrogen gas. The stirring was initiated with 500 RPM at 30° C. and hydrogen gas pressure of 10 kg/cm². The hydrogenation was continued for 48 h. The catalyst was filtered through celite or any other suitable bed and washed with MeOH water (20 ml). The catalyst was recovered for reuse. The filtrate was adjusted to pH 7-7.4 by using glacial acetic acid (~30 ml). The methanol was recovered under reduced pressure at 40° C. The reaction mass was cooled to 0 to 5° C. for 1 h. The solid was filtered on a Buchner funnel using vacuum. The wet cake washed with 20 ml of chilled isopropyl alcohol and suck dried for 30 min. Dry weight of (S)-Pregabalin thus obtained was 14.03 g (74.62% yield; chemical purity 99.94% by HPLC; chiral purity 99.96% by HPLC).

cooled to 0 to 5° C. for 1 h. The solid was filtered on a Buchner funnel using vacuum. The wet cake washed with 60 ml of chilled isopropyl alcohol and suck dried for 30 min. Dry weight of (S)-Pregabalin thus obtained was 19.0 g (67.32% yield; chemical purity 94.33% by HPLC.

Example 6.6: Preparation of S-Pregabalin

To a clean 1 lit autoclave, (S)-3-cyano-5-methyl hexanoic acid methyl ester 20.0 g (1 eq.) was dissolved in methanol (200 ml) at 25° C. A solution of potassium hydroxide (7.69 g in 24 ml water; ~32%) was added by controlling the addition rate to maintain the reaction mass temperature below 25° C. It was stirred at 20-25° C. for about 1.5 h. Raney Ni (6.0 g; 30%) was added. The autoclave was closed properly and started stirring. The air inside the autoclave was replaced by purging nitrogen gas twice. It was pressurized 10 kg/cm² of hydrogen gas and release to atmosphere twice to remove nitrogen gas. The stirring was initiated with

TABLE 8

Recyclability of Raney nickel catalyst

| Batch Size | Conditions | | | | | | Yield |
|---|---|---|---|---|---|---|---|
| g (eq.) GC Purity %, ee | MeOH mL/(V) | KOH (g/eq.) | Raney Ni (W/%) (g) | Pressure (bar) | Temp (° C.) | Time (h) | (g)/(%) HPLC Purity, %, Chiral HPLC Purity |
| 20/(1.0) 99.18 ee: 99.66 | 200/ (10.0) | 7.69/1.16 (32% aq. solution) | 6.0/30 W/% | 10 | 25 30 | 1.5 22 | 14.02/74.53 99.38 R-I: 00.02; S-I: 99.98 |
| 20/(1.0) 99.18 ee: 99.66 | 200/ (10.0) | 7.69/1.16 (32% aq. solution) | Recycle from 1st run | 10 | 25 30 | 1.5 22 | 13.80/73.40 99.69 R-I: 0.03; S-I: 99.97 |
| 20/(1.0) 99.18 ee: 99.66 | 200/ (10.0) | 9.05/1.16 (32% aq. solution) | Recycle from 2nd run | 10 | 30 | 1.5 22 | 13.80/73.40 99.55 R-I: 0.04; S-I: 99.96 |
| 20/(1.0) 99.18 ee: 99.48 | 200/ (10.0) | 9.05/1.16 (32% aq. solution) | Recycle from 3rd run | 10 | 30 | 1.5 22 | 13.00/69.14 97.63 R-I: 0.01; S-I: 99.99 |
| 20/(1.0) 99.11 ee: 99.48 | 200/ (10.0) | 9.05/1.16 (32% aq. solution) | Recycle from 4th run + 1.0/5% | 10 | 30 | 1.5 22 | 13.20/70.21 98.79 R-I: 00.03; S-I: 99.97 |
| 20/(1.0) 99.11 ee: 99.48 | 200/ (10.0) | 9.05/1.16 (32% aq. solution) | Recycle from 5th run | 10 | 30 | 1.5 22 | 11.56/62.02 98.75 R-I: 00.04; S-I: 99.96 |
| 20/(1.0) 99.11 ee: 99.48 | 200/ (10.0) | 9.05/1.16 (32% aq. solution) | Recycle from 6th run + 1.0/5% | 10 | 30 | 1.5 22 | 12.40/66.01 98.43 R-I: 00.03; S-I: 99.97 |

Example 6.5: Preparation of S-Pregabalin

To a clean 1 lit autoclave, (S)-3-cyano-5-methyl hexanoic acid methyl ester 30.0 g (1 eq.) was dissolved in methanol (150 ml) at 25° C. A solution of sodium hydroxide (8.197 g in 25.6 ml water; ~32%) was added by controlling the addition rate to maintain the reaction mass temperature below 25° C. It was stirred at 20-25° C. for about 1.5 h. Raney Ni (9.0 g; 30%; w/w) was added. The autoclave was closed properly and started stirring. The air inside the autoclave was replaced by purging nitrogen gas twice. It was pressurized 10 kg/cm² of hydrogen gas and release to atmosphere twice to remove nitrogen gas. The stirring was initiated with 500 RPM at 30° C. and hydrogen gas pressure of 10 kg/cm². The hydrogenation was continued for 22 h. The catalyst was filtered through celite or any other suitable bed and washed with MeOH water (40 ml). The catalyst was recovered for reuse. The filtrate was adjusted to pH 7-7.4 by using glacial acetic acid (~15 ml). The methanol was recovered under reduced pressure at 40° C. The reaction mass was 500 RPM at 70° C. and hydrogen gas pressure of 10 kg/cm². The hydrogenation was continued for 22 h. The catalyst was filtered through celite or any other suitable bed and washed with MeOH water (30 ml). The catalyst was recovered for reuse. The filtrate was adjusted to pH 7.1±0.1 by using glacial acetic acid (~10 ml). The methanol was recovered under reduced pressure at 40° C. The reaction mass was cooled to 0 to 5° C. for 1 h. The solid was filtered on a Buchner funnel using vacuum. The wet cake washed with 40 ml of chilled isopropyl alcohol and suck dried for 30 min. Dry weight of (S)-Pregabalin thus obtained was 12.7 g (67.51% yield; chemical purity 98.62% by HPLC.

Example 6.7: Preparation of S-Pregabalin

In a 3 neck 1 Lit RBF equipped with mechanical stirrer, thermometer pocket and stopper was taken (S)-3-cyano-5-methyl hexanoic acid methyl ester 60.0 g (1 eq.) and 225.0 ml methanol and cooled to 5-10° C. To this solution was added a solution of 32% aq. potassium hydroxide 84.67 ml (1.16 eq.) by keeping reaction temperature below 10° C. The reaction mixture was stirred at 15-25° C. for 1.5 h. The reaction mass was transferred to a autoclave containing MeOH (225 ml) and Raney Ni 18.0 g (30% w/w). it was hydrogenated at ~40° C. with 350 RPM at 10 kg/cm$^2$ pressure for up to 22 h. Catalyst was filtered. Optionally to the filtrate charcoal (1.5% w/w) was added and stirred for 1 h at room temperature. The mixture was filtered through celite bed and washed with 60 ml methanol. Then the pH was adjusted within the range of 7.1±0.1 by adding glacial acetic acid. Methanol was removed by distillation for at <40° C.) under vacuum followed by MeOH and water mixture at <45° C. and <500 torr vacuum (total distillate collected amounts to 75-85% of the total MeOH and water added. Cool the reaction mixture at 5-10° C. and kept at that temperature for 3 h. The solid was filtered and washed with IPA (120 ml) and suck dried for 3 h at room temperature to get 54.8 g (97.07%) of crude pregabalin with 98.37% HPLC purity. Dissolve the crude pregabalin in refluxing water. The clear solution was distilled till 30-40% solution is obtained. The reaction mixture was cooled at ~25° C. and filtered. It was washed with IPA (45 ml) and dried the solid for 3 h to get 33.0 g of pure Pregabalin (58.0% isolated yield; with 99.14% HPLC purity).

Example 6.8: Preparation of S-Pregabalin

To a clean 1 lit autoclave, (S)-3-cyano-5-methyl hexanoic acid methyl ester 20.0 g (1 eq.) was dissolved in methanol (200 ml) at 25° C. A solution of potassium hydroxide (7.69 g in 24 ml water; ~32%) was added by controlling the addition rate to maintain the reaction mass temperature below 25° C. It was stirred at 20-25° C. for about 1.5 h. Raney Ni (6.0 g; 30%; w/w with respect to substrate) was added. The autoclave was closed properly and started stirring. The air inside the autoclave was replaced by, purging nitrogen gas twice. It was pressurized 5 kg/cm$^2$ of hydrogen gas and release to atmosphere twice to remove nitrogen gas. The stirring was initiated with 500 RPM at 70° C. and hydrogen gas pressure of 5 kg/cm$^2$. The hydrogenation was continued for 22 h. The catalyst was filtered through celite or any other suitable bed and washed with MeOH water (30 ml). The catalyst was recovered for reuse. The filtrate was adjusted to pH 7-7.4 by using glacial acetic acid (~10 ml). The methanol was recovered under reduced pressure at 40° C. The reaction mass was cooled to 0 to 5° C. for 1 h. The solid was filtered on a Buchner funnel using vacuum. The wet cake washed with 40 ml of chilled isopropyl alcohol and suck dried for 30 min. Dry weight of (S)-Pregabalin thus obtained was 12.2 g (64.85% yield; chemical purity 98.63% by HPLC.

Example 6.9: Preparation of S-Pregabalin

To a clean 1 lit autoclave, (5)-3-cyano-5-methyl hexanoic acid methyl ester 30.0 g (1 eq.) was dissolved in methanol (225 ml) at 25° C. A solution of potassium hydroxide (11.53 g in 36 ml water; ~32%) was added by controlling the addition rate to maintain the reaction mass temperature below 25° C. It was stirred at 20-25° C. for about 1.5 h. Raney Ni (9.0 g; 30%; w/w with respect to substrate) was added. The autoclave was closed properly and started stirring. The air inside the autoclave was replaced by purging nitrogen gas twice. It was pressurized 10 kg/cm$^2$ of hydrogen gas and release to atmosphere twice to remove nitrogen gas. The stirring was initiated with 500 RPM at 30° C. and hydrogen gas pressure of 5 kg/cm$^2$. The hydrogenation was continued for 22 h. The catalyst was filtered through celite or any other suitable bed and washed with MeOH water (30 ml). The catalyst was recovered for reuse. The filtrate was adjusted to pH 7-7.4 by using glacial acetic acid (~10 ml). The methanol was recovered under reduced pressure at 40° C. The reaction mass was cooled to 0 to 5° C. for 1 h. The solid was filtered on a Buchner funnel using vacuum and suck dried. The wet cake 23.2 g (82.21%) was suspended in 10% IPA in water (~150 ml) and heated at 90° C. for 2 h. it was cooled to room temperature, filtered and dried. Dry weight of (S)-Pregabalin thus obtained was 16.36 g (58% yield); chemical purity 98.63% by HPLC.

Example 6.10: Preparation of S-Pregabalin

In a 3 neck 1 Lit RBF equipped with mechanical stirrer, thermometer pocket and stopper was taken (S)-3-cyano-5-methyl hexanoic acid methyl ester 200.0 g (1 eq.) and 750.0 ml methanol (3.75 V) and cooled to 5-10° C. To this solution was added a solution of 32% aq. potassium hydroxide 282.0 ml (1.16 eq.) by keeping reaction temperature below 10° C. The reaction mixture was stirred at ~25° C. for 1.5 h. The reaction mass was transferred to a autoclave containing MeOH (750 ml) and Raney Ni 60.0 g (30% w/w). It was hydrogenated at 30° C. with 350 RPM at 10 kg/cm$^2$ pressure for up to 22 h. Catalyst was filtered. Optionally to the filtrate charcoal (1.5% w/w) was added and stirred for 1 h at room temperature. The mixture was filtered through celite bed and washed with 200 ml methanol. Then the pH was adjusted within the range of 7.1±0.1 by adding glacial acetic acid. Methanol was removed by distillation at <40° C.) under vacuum followed by MeOH and water mixture at <45° C. and <500 torr vacuum (total distillate collected amounts to 75-85% of the total MeOH and water added. Cool the reaction mixture at 5-10° C. and kept at that temperature for 3 h. The solid was filtered and washed with IPA (120 ml) and suck dried for 3 h at room temperature to get 155.0 g (82.44%) of crude pregabalin with 94.79% HPLC purity. Dissolve the crude pregabalin in refluxing water. The clear solution was distilled till 30-40% solution is obtained. The reaction mixture was cooled at 25° C. and filtered. It was washed with IPA (200 ml) and dried the solid for 3 h to get 122.0 g of pure Pregabalin (64.8% isolated yield; with 99.85% HPLC purity).

Example 6.11: Preparation of S-Pregabalin

In a 3 neck 1 Lit RBF equipped with mechanical stirrer, thermometer pocket and stopper was taken (S)-3-cyano-5-methyl hexanoic acid methyl ester 60.0 g (1 eq.) and 225.0 ml methanol (3.75 V) and cooled to 5-10° C. To this solution was added a solution of 32% aq. potassium hydroxide 84.67 ml (1.16 eq.) by keeping reaction temperature below 10° C. The reaction mixture was stirred at 15-25° C. for 1.5 h. The reaction mass was transferred to a autoclave containing MeOH (225 ml) and Raney Ni 18.0 g (30% w/w). it was hydrogenated at 30° C. with 350 RPM at 10 kg/cm$^2$ pressure for up to 22 h. Catalyst was filtered. Optionally to the filtrate charcoal (1.5% w/w) was added and stirred for 1 h at room temperature. The mixture was filtered through celite bed and washed with 60 ml methanol. Then the pH was adjusted within the range of 7.1±0.1 by adding glacial acetic acid. Methanol was removed by distillation at <40° C.) under vacuum followed by MeOH and water mixture at <45° C. and 500 torr vacuum (total distillate collected amounts to 75-85% of the total MeOH and water added). Cool the reaction mixture at 5-10° C. and kept at that temperature for 3 h. The solid was filtered and washed with MeOH (60 ml) and suck dried for 3 h at room temperature to get 45.2 g (80.1%) of crude pregabalin with 89.9% HPLC purity. Dissolve the crude pregabalin in refluxing water. The clear solution was distilled till 30-40% solution is obtained. The reaction mixture was cooled at 40° C. and filtered. It was washed with IPA (45 ml) and dried the solid for 3 h to get 34.0 g of pure Pregabalin (60.17% isolated yield; with 99.84% HPLC purity).

Example 6.12: Preparation of S-pregabalin

To a clean 1 lit autoclave, (5)-3-cyano-5-methyl hexanoic acid methyl ester 20.0 g (1 eq.) was dissolved in methanol (200 ml) at 25° C. A solution of potassium hydroxide (7.69 g in 24 ml water; ~32%) was added by controlling the addition rate to maintain the reaction mass temperature below 25° C. It was stirred at 20-25° C. for about 1.5 h. Raney Ni (6.0 g; 30%; w/w with respect to substrate) was added. The autoclave was closed properly and started stirring. The air inside the autoclave was replaced by purging nitrogen gas twice. It was pressurized 10 kg/cm$^2$ of hydrogen gas and release to atmosphere twice to remove nitrogen gas. The stirring was initiated with 500 RPM at 40° C. and hydrogen gas pressure of 10 kg/cm$^2$. The hydrogenation was continued for 22 h. The catalyst was filtered through celite or any other suitable bed and washed with MeOH (30 ml). The catalyst was recovered for reuse. The filtrate was adjusted to pH 7-7.4 by using glacial acetic acid (~10 ml). The methanol was recovered under reduced pressure at 40° C. The reaction mass was cooled to 0 to 5° C. for 1 h. The solid was filtered on a Buchner funnel using vacuum. The wet cake washed with 40 ml of chilled isopropyl alcohol and suck dried for 30 min. Dry weight of (S)-Pregabalin thus obtained was 13.9 g (73.90% yield; chemical purity 96.72% by HPLC.

Example 6.13: Preparation of S-pregabalin

To a clean 1 lit autoclave, (S)-3-cyano-5-methyl hexanoic acid methyl ester 20.0 g (1 eq.) was dissolved in methanol (100 ml) at 25° C. A solution of potassium hydroxide (7.69 g in 24 ml water; ~32%) was added by controlling the addition rate to maintain the reaction mass temperature below 25° C. It was stirred at 20-25° C. for about 1.5 h. Raney Ni (6.0 g; 30%; w/w) was added. The autoclave was closed properly and started stirring. The air inside the autoclave was replaced by purging nitrogen gas twice. It was pressurized 10 kg/cm$^2$ of hydrogen gas and release to atmosphere twice to remove nitrogen gas. The stirring was initiated with 500 RPM at 30° C. and hydrogen gas pressure of 10 kg/cm$^2$. The hydrogenation was continued for 22 h. The catalyst was filtered through celite or any other suitable bed and washed with MeOH (30 ml). The catalyst was recovered for reuse. The filtrate was adjusted to pH 7-7.4 by using glacial acetic acid (~15 ml). The methanol was recovered under reduced pressure at 40° C. The reaction mass was cooled to 0 to 5° C. for 1 h. The solid was filtered on a Buchner funnel using vacuum and suck dried for 30 min to get crude 15.99 g wet Pregabalin. This was transferred into a 250 ml rb flask and 10% aqueous MeOH (~80 ml) was added and heated at 40-50° C. for 2 h. It was cooled to room temperature, filtered and dried. Dry weight of (S)-Pregabalin thus obtained was 13.59 g (72.2% yield; chemical purity 99.71% by HPLC.

Example 6.14: Preparation of S-Pregabalin

To a clean 1 lit autoclave, (S)-3-cyano-5-methyl hexanoic acid methyl ester 250.0 g (1 eq.) was dissolved in methanol (1875 ml) at 25° C. A solution of potassium hydroxide (96.13 g in 300 ml water; ~32%) was added by controlling the addition rate to maintain the reaction mass temperature below 25° C. It was stirred at 20-25° C. for about 1.5 h. Raney Ni (75 g; 30%; w/w) was added. The autoclave was closed properly and started stirring. The air inside the autoclave was replaced by purging nitrogen gas twice. It was pressurized 10 kg/cm$^2$ of hydrogen gas and release to atmosphere twice to remove nitrogen gas. The stirring was initiated with 500 RPM at 30° C. and hydrogen gas pressure of 10 kg/cm$^2$. The hydrogenation was continued for 22 h. The catalyst was filtered through celite or any other suitable bed and washed with MeOH (140 ml). The catalyst was recovered for reuse. The filtrate was adjusted to pH 7-7.4 by using glacial acetic acid (~187.5 ml). The methanol was recovered under reduced pressure at 40° C. The reaction mass was cooled to 0 to 5° C. for 1 h. The solid was filtered on a Buchner funnel using vacuum and suck dried for 30 min to get crude 192.0 g wet Pregabalin. Dissolve the crude pregabalin in refluxing water. The clear solution was distilled till 30-40% solution is obtained. The reaction mixture was cooled at 25° C. and filtered. It was washed with IPA and dried the solid for 3 h to get 158.0 g of pure Pregabalin (67.16% isolated yield; with 99.93% HPLC purity). The MLR of crystallization was concentrated up to half volume by downward distillation at 100-110° C. The mixture was then cooled to 40° C. and then immediately filtered. The IPA cake wash followed stirring in IPA for 1 h at 25-27° C. and filtered. The filtered cake was washed with IPA to afford 10.1 g (4.3%) additional amount of Pregabalin with 99.84% HPLC purity.

Example 6.15: Preparation of S-Pregabalin

To a clean 1 lit autoclave, (S)-3-cyano-5-methyl hexanoic acid methyl ester 70.0 g (1 eq.) was dissolved in methanol (525 ml) at 25° C. A solution of potassium hydroxide (26.91 g in 84 ml water; ~32%) was added by controlling the addition rate to maintain the reaction mass temperature below 25° C. It was stirred at 20-25° C. for about 1.5 h. Raney Ni (21 g; 30%; w/w) was added. The autoclave was closed properly and started stirring. The air inside the autoclave was replaced by purging nitrogen gas twice. It was pressurized 10 kg/cm$^2$ of hydrogen gas and release to atmosphere twice to remove nitrogen gas. The stirring was initiated with 500 RPM at 30° C. and hydrogen gas pressure of 10 kg/cm$^2$. The hydrogenation was continued for 22 h. The catalyst was filtered through celite or any other suitable bed and washed with MeOH. The catalyst was recovered for reuse. The filtrate was adjusted to pH 7-7.4 by using glacial acetic acid. The methanol was recovered under reduced pressure at 40° C. The reaction mass was cooled to 0 to 5° C. for 1 h. The solid was filtered on a Buchner funnel using vacuum and suck dried for 30 min to get crude 46.8 g wet Pregabalin. Dissolve the crude pregabalin in refluxing water. The clear solution was distilled till 30-40% solution is obtained. The reaction mixture was cooled at ~25° C. and filtered. It was washed with IPA and dried the solid for 3 h to get 37.6 g of pure Pregabalin (57.09% isolated yield; with 99.84% HPLC purity). The MLR (200 mL) of crystallization was concentrated up to 60 ml. To the mixture, NaOH (5.26 g) was added and stirred for 5 min. To this suspension, di tert butyl dicarbonate (13.56 g) dissolved in 1,4-dioxane (60 ml) was added and stirred for 2 h at 25-27° C. Completion of the reaction was checked by TLC. The reaction mixture was then concentrated to get a residue. To the residue water was added and extracted with MTBE (30 ml) to remove excess of di tert butyl dicarbonate. The pH of aqueous layer was made pH using citric acid. This mixture was then extracted with ethyl acetate (3×30 ml). The combined organic layer was washed with brine (20 ml) and concentrated to get 7.2 g Boc protected Pregabalin. $^1$H-NMR (DMSO, 400 MHz): δ 12.00 (s, 1H), 6.83 (t, 1H), 2.94 (m, 1H), 2.80 (m, 1H), 2.24-2.19 (dd, 1H), 2.01-1.90 (m, 2H), 1.62 (m, 1H), 1.37 (s, 9H), 1.28 (m, 1H), 1.13 (m, 1H), 0.86 (t, 6H). MS m/z: 258 (M-H)

The following list of some of abbreviations used in the present invention:
Aq: Aqueous
Boc: Tertiary Butyloxycarbonyl
cm$^2$: Square centimeter
DM: Demineralised
DCM: Dichloromethane
DBU: 1,8-Diazabicycloundec-7-ene
DIPA: Diisopropylamine
DMAP: 4-Dimethylaminopyridine
DPA: Diphenylamine
DMF: Dimethyl formamide
DMSO: Dimethyl sulfoxide
ee: Enantiomeric excess
eqv.: Equivalent
EtOAc: Ethyl acetate
g: Gram
GC: Gas chromatography
h: Hour
HPLC: High pressure liquid chromatography
IPA: Isopropyl alcohol
Kg: Kilogram
KotBu: Potassium t-butoxide
KU: Kilo unit
Lit: Liter
MDC: Dichloromethane
MeOH: Methy alcohol
MIBK: Methyl isobutyl ketone
ml: Milliliter
mmol: Milimole
mol: Mole
MTBE: Tertiary Butyl methyl ether
NMR: Nuclear magnetic resonance spectroscopy
RBF: Round bottom flask
RPM: Rotation per minute
THF: Tetrahydrofuran
TLC: Thin layer chromatography
U: Unit
V: Volume

We claim:
1. An improved process for the preparation of a compound of formula (I),

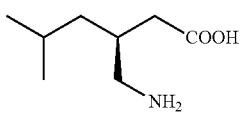

which comprises the steps of:
(a) reacting an isovaleraldehyde of formula (II) and an alkyl cyanoacetate of formula (III) optionally in presence of salts of weak acid and weak base or weak base in a solvent to obtain a 2-cyano-5-methyl-hex-2-enoic acid alkyl ester of formula (IV);

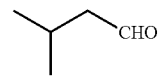

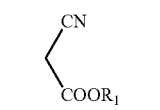

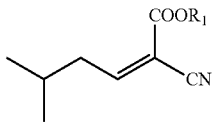

wherein $R_1$ is a linear or branched $C_1$-$C_4$ alkyl;
(b) reacting the 2-cyano-5-methyl-hex-2-enoic acid alkyl ester of formula (IV) with a cyanide source in water or in an organic solvent or mixture thereof to get a 2-isobutylsuccinonitrile of formula (V);

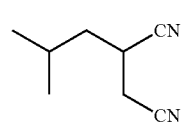

(c) obtaining an optionally substituted 2-isobutylsuccinonitrile of formula (V) by reacting the isovaleraldehyde of formula (II) and the alkyl cyanoacetate of formula (III) in the presence of cyanide source in water or in an organic solvent or mixture thereof in a single step;
(d) converting the 2-isobutylsuccinonitrile of formula (V) to a racemic 3-cyano-5-methyl-hexanoic acid or salt thereof of formula (VI) with a genetically modified nitrilase enzyme Nit 9N_56_2 in water or with an organic co-solvent;

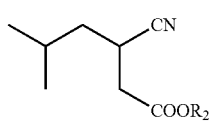

wherein $R_2$ is a cationic counter ion selected from the group consisting of: hydrogen, alkali metal, alkaline earth metal, ammonium, alkyl ammonium, and organic amine;
(e) converting racemic 3-cyano-5-methyl-hexanoic acid or salt thereof of formula (VI) to racemic alkyl 3-cyano-5-methyl-hexanoate of formula (VII) by treatment with alcohol ($R_3$OH) and acidic catalyst or alkyl halide ($R_3$X) in presence of a base;

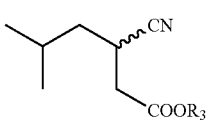

wherein $R_3$ is selected from the group consisting of: a linear or branched $C_1$-$C_4$alkyl, $C_7$-$C_{10}$ aryl, and alkyl aryl;

(f) obtaining an (S)-alkyl 3-cyano-5-methyl-hexanoate of formula (VIII) and (R)-3-cyano-5-methyl-hexanoic acid or salt thereof of formula (X) by enzymatic enantioselective hydrolysis in water or an organic solvent or a mixture thereof from the racemic alkyl 3-cyano-5-methyl-hexanoate of formula (VII), wherein the enzymatic enantioselective hydrolysis is performed using a hydrolysis enzyme selected from the group consisting of: candida Antarctica A, candida Antarctica B1, candida Antarctica BY2, Novozymes, Novozyme 435, lipase 3.101, lipase 3.102, lipase 3.104, lipase 3.105, lipase 3.106, lipase 3.107, lipase 3.108, lipase 3.109, lipase 3.111, lipase 3.115, lipase 3.113, lipase 3.117, lipase 3.136, and any combination thereof;

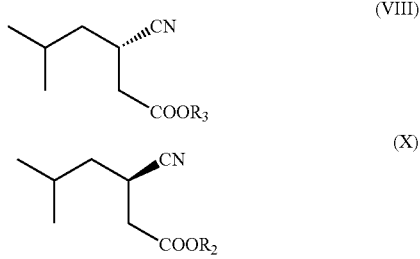

wherein
  $R_2$ is a cationic counter ion selected from the group consisting of: hydrogen, alkali metal, alkaline earth metal, ammonium, alkyl ammonium, and organic amine; and
  $R_3$ is selected from the group consisting of: linear and branched $C_1$-$C_4$ alkyl, $C_7$-$C_{10}$ aryl, and alkyl aryl;
(g) obtaining the compound of formula (VII) by racemizing unwanted (R)-3-cyano-5-methyl-hexanoic acid or salt thereof of formula (X) or substantially enriched (R)-3-cyano-5-methyl-hexanoic acid salt thereof of formula (X) in presence of a base and in a solvent selected from: methyl alcohol, ethyl alcohol, isopropyl alcohol, n-propyl alcohol, n-butyl alcohol, isobutyl alcohol, tertiary butyl alcohol, cyclohexanol, and any combination thereof; and
(h) converting the (S)-alkyl 3-cyano-5-methyl-hexanoate of formula (VIII) to pregabalin of formula (I) by hydrolyzing an ester group with an alkali or alkaline earth metal base followed by hydrogenation in a solvent selected from the group consisting of: water or other organic solvents, and a mixture thereof with a hydrogenation catalyst.

2. The process according to claim 1, wherein the weak acid in step (a) is selected from the group consisting of: benzoic acid, succinic acid, maleic acid, fumaric acid, phthalic acid, and acetic acid; and the weak base in step (a) is selected from the group consisting of: triethyl amine, diisopropylethyl amine, pyridine, piperidine, 1,8-diazabicyclo[5.4.0]undec-7-ene; and the salt used in step (a) is selected from the group consisting of: sodium acetate, ammonium acetate, ammonium benzoate, ammonium succinate, and alkyl ammonium acetate.

3. The process according to claim 1, wherein the solvent in step (a) is selected from the group consisting of: ethyl acetate, dichloromethane, chloroform, methyl tert-butyl ether, cyclohexane, toluene and mixtures thereof, and the organic solvent in steps (b) and (c) is selected from the group consisting of: water, ethyl alcohol, methyl alcohol, isopropyl alcohol, n-butyl alcohol, tetrahydrofuran, dioxane, dimethylformamide, dimethyl sulfoxide, dimethylacetamide, methyl tert-butyl ether, cyclohexane, water and mixtures thereof.

4. The process according to claim 1, wherein the cyanide source of step (b) and step (c) is selected from the group consisting of: lithium cyanide, sodium cyanide, potassium cyanide, and trimethylsilyl cyanide; and wherein the reaction of step (b) is carried out at a temperature range between 45° C. to 120° C.; and the reaction of steps (a) and (c) are carried out at ambient temperature to reflux temperature.

5. The process according to claim 1, wherein a loading of compound of formula (V) for the preparation of compound (VI) in step (d) is chosen from 30 to 300 g per liter of water or water in combination of co-solvent; and a loading of genetically modified nitrilase enzyme (Nit 9N_56_2) for the preparation of compound (VI) in step (d) is chosen from 4 to 25 U per g of compound (V); and a pH is kept in a range of 7.2±0.8 and maintained by a buffer selected from phosphate or acetate buffer or by addition of an acid chosen from among acetic, citric, tartaric, hydrochloric, sulfuric, phosphoric acid and a base which is selected from the group consisting of: ammonia, mono, di and tri alkyl amine, sodium hydroxide, sodium carbonate, potassium carbonate, sodium bicarbonate, and potassium bicarbonate; and step (d) is carried out at a temperature range between 25° C. to 40° C.

6. The process according to claim 1, wherein the alcohol ($R_3OH$) in step (e) is selected from the group consisting of methyl alcohol, ethyl alcohol, isopropyl alcohol, n-propyl alcohol, n-butyl alcohol, cyclopentanol, and cyclohexanol; and the alkyl halide ($R_3X$) in step (e) is selected from the group consisting of: methyl iodide, ethyl chloride, ethyl bromide, ethyl iodide, n-propyl bromide, isopropyl chloride, and isopropyl bromide; and the acid catalyst or reagent in step (e) is selected from the group consisting of hydrochloric acid, sulfuric acid, thionyl chloride, trimethylsilyl chloride, methanesulfonic acid, paratoluene sulfonic acid, benzene sulfonic acid, trifluoromethanesulfonic acid, Lewis acid or strongly acidic sulfonated resins.

7. The process according to claim 1, wherein during the preparation of the racemic alkyl 3-cyano-5-methyl-hexanoate of formula (VII), the same is purified by distillation in step (e).

8. The process according to claim 1, wherein the solvent in step (f) is selected from the group consisting of: water, methyl alcohol, ethyl alcohol, isopropyl alcohol, n-butyl alcohol, isobutyl alcohol, acetone, methyl isobutyl ketone, acetonitrile, methyl tert-butyl ether, tetrahydrofuran, 2-methyl tetrahydrofuran, 1,4-dioxane, and dimethyl sulfoxide; and an initial pH of a solution of step (f) is kept in a range of 7.5±0.5 by using a reagent selected from the group consisting of: acetic acid, citric acid, boric acid, ethylenediaminetetraacetic acid, hydrochloric acid, sulfuric acid, triethyl amine, diisopropylamine, pyridine, sodium bicarbonate, potassium bicarbonate, sodium carbonate, potassium carbonate, calcium carbonate, calcium hydroxide, magnesium hydroxide, magnesium oxide, and any combination thereof; and the initial pH of the solution of step (f) during reaction is allowed to increase in the range of 7 to 9.

9. The process according to claim 1, wherein the conversion of racemic alkyl 3-cyano-5-methyl-hexanoate of formula (VII) to substantially enantiopure (S)-ester (VIII) in step (f), the enzymatic enantioselective hydrolysis is carried out in presence of salts which can be selected from the group consisting of lithium chloride, sodium chloride, potassium chloride, calcium chloride, and magnesium chloride or generated in situ by neutralization of an acid and a base; and the enzymatic enantioselective hydrolysis of step (f) is carried out at a temperature range between 20° C. to 45° C.

10. The process according to claim 1, wherein the solvent in steps (g) and (h) are selected from the group consisting of water, methyl alcohol, ethyl alcohol, isopropyl alcohol, n-propyl alcohol, n-butyl alcohol, isobutyl alcohol, tertiary butyl alcohol, cyclohexanol, toluene, monochlorobenzene, dichlorobenzene, tetrahydrofuran, 2-methyl tetrahydrofuran, 1,4-dioxane, dimethylformamide, dimethyl amine, dimethyl sulfoxide, sulfolane, and any combinations thereof.

11. The process according to claim 1, wherein the base used in step (g) is selected from the group consisting of: triethyl amine, diisopropylethyl amine, pyridine, piperidine, 1,8-diazabicyclo[5.4.0]undec-7-ene, 1,4-diazabicyclo[2.2.2] octane, sodium bicarbonate, potassium bicarbonate, sodium carbonate, potassium carbonate, and alkali and alkaline earth metal $C_1$-$C_6$ alkoxides; and the step (g) is carried out at a temperature range between 25° C. to 200° C. for 1 to 60 hours; and the base for hydrolysis in step (h) is selected from alkali or alkaline earth metal hydroxides selected from the group consisting of: lithium hydroxide, sodium hydroxide, potassium hydroxide, calcium hydroxide, magnesium hydroxide, barium hydroxide, and $C_1$-$C_5$ quaternary ammonium hydroxide.

12. The process according to claim 1, wherein the step (h) comprises in-situ hydrolysis of the compound of structure (VIII) followed by catalytic hydrogenation wherein a base strength for hydrolysis is selected from 0.1N to 5N; and the hydrogenation catalyst is selected from the group consisting of: nickel, palladium, ruthenium, rhodium, with or without support, and any chemical forms and grades; and the catalysis is carried out at a temperature range between 10° C. to 100° C. with a hydrogen pressure in a range of 0.5 to 25 $kg/cm^2$.

13. The process according to claim 1, wherein the preparation of the compound of formula (I) comprises charcoalization of hydrogenation product and isolation of pregabalin by isoelectric focusing in a pH range of 6.9 to 7.3 and crystallization of crude material from water, $C_1$-$C_5$ alcohol or a mixture thereof; and the pH is adjusted with any inorganic or organic acid selected from the group consisting of: hydrochloric acid, sulfuric acid, acetic acid, phosphoric acid, formic acid, and trifluoroacetic acid; and further recovering the pure pregabalin of formula (I) by recrystallization of a dried mother liquor.

14. The process according to claim 13, wherein the preparation of the compound of formula (I) further comprises alternative recovery of pregabalin of formula (I) from the mother liquor as an amino protecting derivative selected from the group consisting of: tert-butyloxycarbonyl, carboxybenzyl, and trityl and subsequent removal of tert-butyloxycarbonyl group by treatment with acid in a solvent.

* * * * *